(12) United States Patent
Bisbee, III et al.

(10) Patent No.: US 9,345,591 B2
(45) Date of Patent: May 24, 2016

(54) CONTROL SYSTEM AND METHOD FOR A PROSTHETIC KNEE

(71) Applicant: Össur hf, Reykjavik (IS)

(72) Inventors: Charles R Bisbee, III, Mission Viejo, CA (US); Scott B Elliott, San Clemente, CA (US); Magnus Oddsson, Hafnarfjordur (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/081,965

(22) Filed: Nov. 15, 2013

(65) Prior Publication Data

US 2014/0156025 A1 Jun. 5, 2014

Related U.S. Application Data

(60) Continuation of application No. 12/692,438, filed on Jan. 22, 2010, now Pat. No. 8,617,254, which is a division of application No. 11/077,177, filed on Mar. 9, 2005, now abandoned.

(60) Provisional application No. 60/572,996, filed on May 19, 2004, provisional application No. 60/569,511, filed on May 7, 2004, provisional application No. 60/551,717, filed on Mar. 10, 2004.

(51) Int. Cl.
*A61F 2/68* (2006.01)
*A61F 2/64* (2006.01)
(Continued)

(52) U.S. Cl.
CPC ... *A61F 2/68* (2013.01); *A61F 2/64* (2013.01); *A61F 2002/5003* (2013.01); *A61F 2002/5004* (2013.01); *A61F 2002/5033* (2013.01); *A61F 2002/6863* (2013.01); *A61F 2002/704* (2013.01); *A61F 2002/705* (2013.01); *A61F 2002/764* (2013.01); *A61F 2002/7625* (2013.01); *A61F 2002/7635* (2013.01); *A61F 2250/0034* (2013.01)

(58) Field of Classification Search
CPC ............... A61F 2/28; A61F 2/68; A61F 2/64; G06F 3/0481
See application file for complete search history.

(56) References Cited

U.S. PATENT DOCUMENTS 2,568,051 A 9/1951 Catranis
3,820,168 A 6/1974 Horvath
(Continued)

FOREIGN PATENT DOCUMENTS

CN 1678258 10/2005
DE 35 43 291 6/1987
(Continued)

OTHER PUBLICATIONS

Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.
(Continued)

*Primary Examiner* — Jason-Dennis Stewart
(74) *Attorney, Agent, or Firm* — Knobbe, Martens, Olson & Bear, LLP

(57) ABSTRACT

A prosthetic or orthotic system including a magnetorheological (MR) damper. The MR damper may be configured to operate in shear mode. In one embodiment, the MR damper includes a rotary MR damper. A controller is configured to operate the damper. A mobile computing device may be adapted to intermittently communicate configuration parameters to the controller. A method of configuring a prosthetic or orthotic system is also disclosed.

10 Claims, 12 Drawing Sheets

(51) Int. Cl.
    *A61F 2/50* (2006.01)
    *A61F 2/70* (2006.01)
    *A61F 2/76* (2006.01)

(56) References Cited

U.S. PATENT DOCUMENTS

| | | | |
|---|---|---|---|
| 3,866,246 A | 2/1975 | Seamone et al. |
| 3,995,324 A | 12/1976 | Burch |
| 4,005,496 A | 2/1977 | Wilkes |
| 4,030,141 A | 6/1977 | Graupe |
| 4,064,569 A | 12/1977 | Campbell |
| 4,065,815 A | 1/1978 | Sen-Jung |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,569,352 A | 2/1986 | Petrofsky et al. |
| 4,685,927 A | 8/1987 | Haupt |
| 4,711,242 A | 12/1987 | Petrofsky |
| 4,711,450 A | 12/1987 | McArthur |
| 4,760,850 A | 8/1988 | Phillips et al. |
| 4,770,662 A | 9/1988 | Giampapa |
| 4,776,852 A | 10/1988 | Bubic |
| 4,790,522 A | 12/1988 | Drutchas |
| 4,808,187 A | 2/1989 | Patterson et al. |
| 4,854,428 A | 8/1989 | Horvath |
| 4,876,944 A | 10/1989 | Wilson et al. |
| 4,878,913 A | 11/1989 | Aebischer et al. |
| 4,893,648 A | 1/1990 | Horvath |
| 4,919,418 A | 4/1990 | Miller |
| 4,958,705 A | 9/1990 | Horvath |
| 4,994,086 A | 2/1991 | Edwards |
| 5,020,790 A | 6/1991 | Beard et al. |
| 5,044,360 A | 9/1991 | Janke |
| 5,062,856 A | 11/1991 | Sawamura et al. |
| 5,062,857 A | 11/1991 | Berringer |
| 5,092,902 A | 3/1992 | Adams et al. |
| 5,112,296 A | 5/1992 | Beard et al. |
| 5,112,356 A | 5/1992 | Harris et al. |
| 5,139,525 A | 8/1992 | Kristinsson |
| 5,153,496 A | 10/1992 | LaForge |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,252,102 A | 10/1993 | Singer et al. |
| 5,253,656 A | 10/1993 | Rincoe et al. |
| 5,265,890 A | 11/1993 | Balsells |
| 5,277,281 A | 1/1994 | Carlson et al. |
| 5,284,330 A | 2/1994 | Carlson et al. |
| 5,336,269 A | 8/1994 | Smits |
| 5,376,128 A | 12/1994 | Bozeman, Jr. |
| 5,376,133 A | 12/1994 | Gramnaes |
| 5,376,137 A | 12/1994 | Shorter et al. |
| 5,382,373 A | 1/1995 | Carlson et al. |
| 5,383,939 A | 1/1995 | James |
| 5,397,287 A | 3/1995 | Lindfors |
| 5,398,917 A | 3/1995 | Carlson et al. |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,458,655 A | 10/1995 | Bozeman, Jr. |
| 5,472,412 A | 12/1995 | Knoth |
| 5,476,441 A | 12/1995 | Durfee et al. |
| 5,480,454 A | 1/1996 | Bozeman, Jr. |
| 5,484,389 A | 1/1996 | Stark et al. |
| 5,504,415 A | 4/1996 | Podrazhansky et al. |
| 5,545,232 A | 8/1996 | Van de Veen |
| 5,545,233 A | 8/1996 | Fitzlaff |
| 5,571,205 A | 11/1996 | James |
| 5,571,212 A | 11/1996 | Cornelius |
| 5,571,213 A | 11/1996 | Allen |
| 5,586,557 A | 12/1996 | Nelson et al. |
| 5,624,389 A | 4/1997 | Zepf |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| 5,662,693 A | 9/1997 | Johnson et al. |
| 5,670,077 A | 9/1997 | Carlson et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer |
| 5,749,533 A | 5/1998 | Daniels |
| 5,755,813 A | 5/1998 | Krukenberg |
| 5,779,735 A | 7/1998 | Molino |
| 5,800,568 A | 9/1998 | Atkinson et al. |
| 5,823,309 A | 10/1998 | Gopalswamy et al. |
| 5,842,547 A | 12/1998 | Carlson et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,246 A | 3/1999 | Gow |
| 5,893,891 A | 4/1999 | Zahedi |
| 5,895,430 A | 4/1999 | O'Connor |
| 5,900,184 A | 5/1999 | Weiss et al. |
| 5,906,767 A | 5/1999 | Karol et al. |
| 5,919,149 A | 7/1999 | Allum |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Gramnaes |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| RE36,521 E | 1/2000 | Hiemisch |
| 6,027,664 A | 2/2000 | Weiss et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,766 A | 10/2000 | Johnson et al. |
| 6,139,586 A | 10/2000 | Wagner et al. |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | Gerad van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |

(56) References Cited

U.S. PATENT DOCUMENTS

| | | |
|---|---|---|
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,587,728 B2 | 7/2003 | Fang et al. |
| 6,602,295 B1 | 8/2003 | Doddroe et al. |
| 6,610,101 B2 | 8/2003 | Herr et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,719,806 B1 | 4/2004 | Zahedi et al. |
| 6,740,123 B2 | 5/2004 | Davalli et al. |
| 6,743,260 B2 | 6/2004 | Townsend et al. |
| 6,755,870 B1 | 6/2004 | Biedermann et al. |
| 6,764,520 B2 | 7/2004 | Deffenbaugh et al. |
| 6,780,343 B2 | 8/2004 | Hata et al. |
| 6,855,170 B2 | 2/2005 | Gramnäs |
| 6,875,241 B2 | 4/2005 | Christesen |
| 6,876,135 B2 | 4/2005 | Pelrine |
| 6,908,488 B2 | 6/2005 | Passivaara et al. |
| 6,918,308 B2 | 7/2005 | Biedermann |
| 6,955,692 B2 | 10/2005 | Grundei |
| 6,966,882 B2 | 11/2005 | Horst |
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,101,487 B2 | 9/2006 | Hsu et al. |
| 7,118,601 B2 | 10/2006 | Yasui |
| 7,131,998 B2 | 11/2006 | Pasolini |
| 7,137,998 B2 | 11/2006 | Bédard et al. |
| 7,147,667 B2 | 12/2006 | Bédard et al. |
| 7,164,967 B2 | 1/2007 | Etienne-Cummings et al. |
| 7,198,071 B2 | 4/2007 | Bisbee, III et al. |
| 7,279,009 B2 | 10/2007 | Herr |
| 7,308,333 B2 | 12/2007 | Kern et al. |
| 7,313,463 B2 | 12/2007 | Herr et al. |
| 7,314,490 B2 | 1/2008 | Bédard et al. |
| 7,455,696 B2 | 11/2008 | Bisbee, III et al. |
| 7,503,900 B2 | 3/2009 | Goswami |
| 7,520,904 B2 | 4/2009 | Christensen |
| 7,531,006 B2 | 5/2009 | Clausen et al. |
| 7,588,604 B2 | 9/2009 | Okuda |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,736,394 B2 | 6/2010 | Bédard et al. |
| 7,799,091 B2 | 9/2010 | Herr et al. |
| 7,811,334 B2 | 10/2010 | Ragnarsdottir et al. |
| 7,815,689 B2 | 10/2010 | Bédard et al. |
| 7,867,284 B2 | 1/2011 | Bédard et al. |
| 7,867,285 B2 | 1/2011 | Clausen et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bédard et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,231,687 B2 | 7/2012 | Bédard et al. |
| 8,435,309 B2 | 5/2013 | Gilbert et al. |
| 7,431,737 C1 | 12/2013 | Ragnarsdottir et al. |
| 8,617,254 B2 | 12/2013 | Bisbee, III et al. |
| 8,657,886 B2 | 2/2014 | Clausen et al. |
| 2002/0087216 A1 | 7/2002 | Atkinson et al. |
| 2002/0103543 A1 | 8/2002 | Asai et al. |
| 2002/0161451 A1* | 10/2002 | Biedermann et al. ........... 623/27 |
| 2003/0019700 A1 | 1/2003 | Wittig |
| 2004/0064195 A1 | 4/2004 | Herr |
| 2004/0078299 A1* | 4/2004 | Down-Logan et al. ......... 705/27 |
| 2004/0153484 A1 | 8/2004 | Unno |
| 2004/0217324 A1 | 11/2004 | Hsu et al. |
| 2005/0107889 A1 | 5/2005 | Bédard et al. |
| 2005/0283257 A1 | 12/2005 | Bisbee et al. |
| 2006/0136072 A1 | 6/2006 | Bisbee et al. |
| 2006/0184252 A1 | 8/2006 | Oddsson et al. |
| 2006/0184280 A1 | 8/2006 | Oddsson et al. |
| 2006/0249315 A1 | 11/2006 | Herr et al. |
| 2007/0043449 A1 | 2/2007 | Herr et al. |
| 2007/0050047 A1 | 3/2007 | Ragnarsdottlr et al. |
| 2007/0123997 A1 | 5/2007 | Herr et al. |
| 2007/0162152 A1 | 7/2007 | Herr et al. |
| 2008/0046096 A1 | 2/2008 | Bédard et al. |
| 2010/0131101 A1 | 5/2010 | Engeberg et al. |
| 2010/0262260 A1 | 10/2010 | Bédard et al. |
| 2011/0106274 A1 | 5/2011 | Ragnarsdottir et al. |
| 2011/0224804 A1 | 9/2011 | Clausen et al. |

FOREIGN PATENT DOCUMENTS

| | | |
|---|---|---|
| DE | 43 05 213 | 8/1993 |
| DE | 43 18 901 | 1/1994 |
| DE | 42 29 330 | 3/1994 |
| DE | 195 21 464 | 3/1997 |
| DE | 197 54 690 | 7/1999 |
| DE | 19754690 A1 | 7/1999 |
| EP | 0 380 060 | 8/1990 |
| EP | 0380060 A3 | 4/1992 |
| EP | 0 503 775 | 9/1992 |
| EP | 0 549 855 | 7/1993 |
| EP | 0 628 296 | 12/1994 |
| EP | 0 718 951 | 6/1996 |
| EP | 0 902 547 | 3/1999 |
| EP | 0 957 838 | 11/1999 |
| EP | 1 066 793 | 1/2001 |
| EP | 1 125 825 | 1/2001 |
| EP | 1 107 420 | 6/2001 |
| EP | 1 166 726 | 1/2002 |
| EP | 1 169 982 | 1/2002 |
| EP | 1 340 478 | 9/2003 |
| EP | 1 613 872 | 4/2007 |
| FR | 2 623 086 | 5/1989 |
| FR | 2 816 463 | 5/2002 |
| GB | 2 201 260 | 8/1988 |
| GB | 2 244 006 | 11/1991 |
| GB | 2 260 495 | 4/1993 |
| GB | 2 301 776 | 12/1996 |
| GB | 2 302 949 | 2/1997 |
| GB | 2 328 160 | 2/1999 |
| GB | 2 334 891 | 9/1999 |
| GB | 2 338 653 | 12/1999 |
| GB | 2 367 753 | 4/2002 |
| JP | 59-088147 | 5/1984 |
| JP | 59-189843 | 10/1984 |
| JP | 60-081530 | 5/1985 |
| JP | 03-181633 | 8/1991 |
| JP | 04-078337 | 3/1992 |
| JP | 11-000345 | 1/1999 |
| JP | 11-056885 | 3/1999 |
| JP | 2001-277175 | 10/2001 |
| JP | 2002-191654 | 7/2002 |
| JP | 2003-250824 | 9/2003 |
| JP | 2005-500 | 1/2005 |
| JP | 2005-536317 | 12/2005 |
| WO | WO 94/06374 | 3/1994 |
| WO | WO 95/26171 | 10/1995 |
| WO | WO 96/39110 | 12/1996 |
| WO | WO 96/41598 | 12/1996 |
| WO | WO 96/41599 | 12/1996 |
| WO | WO 97/00661 | 1/1997 |
| WO | WO 97/04396 | 2/1997 |
| WO | WO 98/25552 | 6/1998 |

(56) References Cited

FOREIGN PATENT DOCUMENTS

| WO | WO 98/38951 | 9/1998 |
|----|----|----|
| WO | WO 99/05991 | 2/1999 |
| WO | WO 99/08621 | 2/1999 |
| WO | WO 99/11206 | 3/1999 |
| WO | WO 99/29272 | 6/1999 |
| WO | WO 00/30572 | 6/2000 |
| WO | WO 00/38599 | 7/2000 |
| WO | WO 00/71061 | 11/2000 |
| WO | WO 01/17466 | 3/2001 |
| WO | WO 01/50986 | 7/2001 |
| WO | WO 01/54630 | 8/2001 |
| WO | WO 01/72245 | 10/2001 |
| WO | WO 02/080825 | 10/2002 |
| WO | WO 03/003953 | 1/2003 |
| WO | WO 03/086245 | 10/2003 |
| WO | WO 03/088373 | 10/2003 |
| WO | WO 2004/017871 | 3/2004 |
| WO | WO 2004/017872 | 3/2004 |
| WO | WO 2004/017873 | 3/2004 |
| WO | WO 2005/041819 | 5/2005 |
| WO | WO 2005/079712 | 9/2005 |
| WO | WO 2005/087144 | 9/2005 |
| WO | WO 2008/080232 | 7/2008 |
| WO | WO 2008/080233 | 7/2008 |
| WO | WO 2008/080234 | 7/2008 |
| WO | WO 2008/086629 | 7/2008 |

OTHER PUBLICATIONS

Martin, C.W., Otto Bock C-leg: A Review of Its Effectiveness, WCB Evidence Based Group, Nov. 27, 2003.

Moe-Nilssen, R.; "A New Method for Evaluating Motor Control in Gait Under Real-Life Environmental Conditions. Part 1: The Instrument" Clinical Biomechanics, vol. 13, 1998, pp. 320-327.

Moe-Nilssen, R.; "A New Method for Evaluating Motor Control in Gait Under Real-Life Environmental Conditions. Part 2: Gait Analysis" Clinical Biomechanics, vol. 13, 1998, pp. 328-335.

"The Electronic C-Leg® Knee Joint System," Instructions for Use, Otto Bock®, 2002, pp. 30. http://www.ottobockus.com/products/lower_limb_prosthetics/c-leg_instructions.pdg (printed Jul. 20, 2006) Asserted by iWalk in Civil Action No. 12-CV-11061 FDS to constitute prior art to U.S. Pat. Nos. 7,431,737 and 7,896,927. Applicant requests that the Examiner to consider this reference as qualifying as prior art to the present application, but reserves the right to challenge the reference's prior art status at a later date.

Van Der Kooij, H., et al., A Multisensory Integration Model of Human Stance Control, Biol. Cybern. 80:299-308, 1998.

Tomović et al., "A Finite State Approach to the Synthesis of Bioengineering Control Systems," IEEE Transactions of Human Factors in Electronics, vol. HFE-7, No. 2, Jun. 1966, pp. 65-69.

Aminian et al., "Estimation of Speed and Incline of Walking Using Neural Network," IEEE Transactions on Instrumentation and Measurement, vol. 44, No. 3, Jun. 1995, pp. 743-746.

Popovic et al., "Control Aspects of Active Above-Knee Prosthesis," International Journal of Man-Machine Studies, vol. 35, No. 6, Dec. 1991, pp. 751-767.

Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.

Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.

Tong et al., "A Practical Gait Analysis System Using Gyroscopes," Medical Engineering and Physics, vol. 21, 1999, pp. 87-94.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to consitute prior art to U.S. Pat. Nos. 7,431,737 and 7,896,927. Applicant requests that the Examiner to consider this reference as qualifying as prior art to the present application, but reserves the right to challenge the reference's prior art status at a later date.

Andrews et al., "Hybrid FES Orthosis Incorporating Closed Loop Control and Sensory Feedback," Journal of Biomedical Engineering, vol. 10, Apr. 1988, pp. 189-195.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.

Petrofsky et al., "Feedback Control System for Walking in Man," Computers in Biology and Medicine, vol. 14, No. 2, pp. 135-149, 1984.

Smidt et al., "An Automated Accelerometry System for Gait Analysis," Journal of Biomechanics, vol. 10, 1977, pp. 367-375.

Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.

Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

Willemsen et al., "Real-Time Gait Assessment Utilizing a New Way of Accelerometry," Journal of Biomechanics, vol. 23, No. 8, 1990. pp. 859-863.

Dai et al., "Application of Tilt Sensors in Functional Electrical Stimulation," IEEE Transactions on Rehabilitation Engineering, vol. 4, No. 2, Jun. 1996, pp. 63-72.

Reitman et al., "Gait Analysis in Prosthetics: Opinions, Ideas, and Conclusions," Prosthetics and Orthotics International, vol. 26, 2002, 50-57.

Foerster et al., "Detection of Posture and Motion by Accelerometry: A Validation Study in Ambulatory Monitoring," Computers in Human Behavior, vol. 15, 1999, pp. 571-583.

Sekine et al., "Classification of Waist-Acceleration Signals in a Continuous Walking Record," Medical Engineering & Physics, 2000, pp. 285-291.

Tong et al., "Virtual Artificial Sensor Technique for Functional Electrical Stimulation," Medical Engineering & Physics, vol. 20, 1998, pp. 458-468.

Veltink et al., "Detection of Static and Dynamic Activities using Uniaxial Accelerometers," IEEE Transactions on Rehabilitation Engineering, vol. 4, No. 4, Dec. 1996, pp. 375-385.

Jonic et al., "Three Machine Learning Techniques for Automatic Determination of Rules to Control Locomotion," IEEE, Transactions on Biomedical Engineering, vol. 46, No. 3, Mar. 1999, pp. 300-310.

Kostov et al., "Machine Learning in Control of Functional Electrical Stimulation Systems for Locomotion," IEEE Transactions on Biomedical Engineering, vol. 42, No. 6, Jun. 1995, pp. 541-551.

Kirkwood et al., "Automatic Detection of Gait Events: A Case Study Using Inductive Learning Techniques," Journal of Biomedical Engineering, vol. 11, Nov. 1989, pp. 511-516.

Bar et al., "Adaptive Microcomputer Control of an Artificial Knee in Level Walking," Journal of Biomechanical Engineering, vol. 5, Apr. 1983, pp. 145-150.

Lee et al., "Activity and Location Recognition Using Wearable Sensors," Pervasive Computing, Jul.-Sep. 2002, pp. 24-32.

Frank et al., "Reliable Real-Time Recognition of Motion Related Human Activities Using MEMS Inertial Sensors," 2010, http://www.xsens.com/images/stories/PDF/Activity_Recognition_Final_ION_2010_Paper.pdf.

Office Action in Canadian Patent Application No. 2559890, dated Aug. 25, 2011.

Office Action in Canadian Patent Application No. 2559890, dated Jun. 11, 2012.

Office Action in European Patent Application No. 05725431, dated Sep. 23, 2010 in 5 pages.

(56) References Cited

OTHER PUBLICATIONS

International Search Report in International Application No. PCT/US2005/008243, dated Oct. 10, 2005 in 5 pages.
International Preliminary Report on Patentability and Written Opinion in International Application No. PCT/US2005/008243, dated Sep. 21, 2006 in 10 pages.
Au et al., "An EMG-Position Controlled System for an Active Ankle-Foot Prosthesis: An Initial Experimental Study," Proceeding of the 2005 IEEE 9th International Conference on Rehabilitation Robotics, Chicago, IL, Jun. 28-Jul. 1, 2005, pp. 375-379.
Blumentritt et al., "Design Principles, Biomedical Data and Clinical Experience with a Polycentric Knee Offering Controlled Stance Phase Knee Flexion: A Preliminary Report", Journal of Prosthetics and Orthotics, vol. 9, No. 1, Winter 1997, pp. 18-24.
Carlson et al., "Commercial Magneto-Rheological Fluid Devices," International Journal of Modern Physics B, vol. 10, No. 23-24, Oct. 30, 1996, pp. 8.
Carlson et al., "Smart Prosthetics Based on Magnetorheological Fluids," 8th Annual Symposium on Smart Structures and Materials, Newport Beach, CA, Mar. 2001, pp. 9.
Carlson, J. David; "What makes a Good MR Fluid?" 8th International Conference on Electrorheological (ER) Fluids and magneto-rheological (MR) Suspensions, Nice, Jul. 9-13, 2001, pp. 7.
Copes Inc., "Copes/Bionic Ankle," The Most Significant Development in Ankle Prosthetics in Over a Half Century, Brochure, Nov. 1985, pp. 3.
Dietl et al., "Der Einsatz von Elektronik bei Prothesen zur Versorgung der unteren Extremität," Med. Orth. Tech., vol. 117, 1997, pp. 31-35.
Elliott, Scott B.; "MR Microprocessor-Controlled Swing and Stance," Presentation to American Academy of Orthotists & Prosthetics (Feb. 4, 2004), 81 pages.
Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.
Herr et al., "User-Adaptive Control of a Magnetorheological Prosthetic Knee," Industrial Robot: An International Journal, vol. 30, No. 1, 2003. pp. 42-55.
Herr, Hugh; "Experiencing the Frontiers of Biomedical Technology," Presentation, Harvard-MIT Division of Health Sciences & Technology, Mar. 10-11, 2003, Harvard Medical School, p. 1.
Invitation to Pay Fees and Partial International Search Report in International Application No. PCT/US2005/008243, dated Jul. 22, 2005.
International Preliminary Report on Patentability and Written Opinion in PCT Application No. PCT/US2005/004878, mailed Aug. 24, 2006.
Kirsner, Scott; "A Step in the Right Direction Biomedical Horizons Expanding," Boston Globe, Mar. 17, 2003, pp. 4.
Lelas et al., "Hydraulic Versus Magnetorheological-Based Electronic Knee Prostheses: A Clinical Comparison," Massachusetts, 2004, pp. 1-16.
Ossur Academy, 2004 Course Descriptions, Ossur North America, 16 pages.
Otto Bock®, "C-LEG: A New Dimension in Amputee Mobility," Otto Bock Data Sheet, Otto Bock Orthopadische Industrie, 1997, pp. 4.
"C-Leg Fitting Statistics," Abstract, Otto Bock Orthopädische Industrie GmbH & Co., Mar. 2000, pp. 4.
Otto Bock, Modular Knee Joints, http://www.healthcare.ottobock.com/technical_orthopedics/beinprothesen/sites/knee.htm, printed Jul. 10, 2002, 4 pages.
Otto Bock, Quality for Life, Software C-Soft, Menu-driven setting of the C-Leg, 2004 1 page.
Otto, Judith, "Prosthetic Knees: What's on the Way?", The O&P edge, http://www.oandp.com/edge/issues/ articles/2003 -10_02 .asp, Oct. 2003, 5 pages.
Popovic et al., "Optimal Control for an Above-Knee Prosthesis With Two Degrees of Freedom," Journal of Biomechanics, vol. 28, No. 1, 1995, pp. 89-98.
Proteor, "Assembly and Adjustment Instructions for IP50-R," Sep. 2004, pp. 1-21.
Schmalz et al., "Energy Efficiency of Trans-Femoral Amputees Walking on Computer-Controlled Prosthetic Knee Joint 'C-Leg,'" International Society for Prosthetics and Orthotics: Conference Book 9th World ISPO-World Congress, 1998, pp. 3.
"State-of-the-Art Prosthetic Leg Incorporates Magneto-Rheological Technology," Medical Product Manufacturing News, Nov. 2000, p. 42 [Web version attached in 3 pages].
Suga et al., "Newly Designed Computer Controlled Knee-Ankle-Foot Orthosis (Intelligent Orthosis)", Prosthetics and Orthotics International, vol. 22, 1998, pp. 230-239.
Thakkar, Sneha, "Energy Economy Gait Analysis of an Autoadaptive Prosthetic Knee," Massachusetts Institute of Technology, Thesis, Aug. 30, 2002 in 58 pages.
Townsend et al., "Biomechanics and Modeling of Bipedal Climbing and Descending," Journal of Biomechanics, vol. 9, No. 4, 1976, pp. 227-239.
Van der Loos et al., "ProVAR Assistive Robot System Architecture," Proceedings of the 1999 IEEE International Conference on Robotics & Automation, Detroit, Michigan, vol. 1, May 1999, pp. 741-746.
Wilkenfeld, Ari J, Ph.D.; "An Auto-Adaptive External Knee Prosthesis," Artificial Intelligence Laboratory, MIT, Sep. 2000, pp. 3.
Wilkenfeld, Ari J, Ph.D.; "Biologically Inspired Autoadaptive Control of a Knee Prosthesis," Massachusetts Institute of Technology, Thesis, Jul. 2000, (believed to be catalogued on or after Oct. 23, 2000) in 106 pages.
Zamiska, Nicholas, Bionic Knee 'Learns' How to Walk, 1 page, The Wall Street Journal, Jul. 6, 2004.
Bonivento, Claudio et al., "Automatic Tuning of Myoelectric Prostheses," Journal of Rehabilitation Research and Development, Jul. 1998, vol. 35, No. 3, pp. 294-304.
Michael, John W., "Upper Limb Powered Components and Controls: Current Concepts," The American Academy of Orthotists & Prosthetists, 1986, vol. 10, No. 2, pp. 66-77.

* cited by examiner

CONTROL SYSTEM AND METHOD FOR A PROSTHETIC KNEE

RELATED APPLICATIONS

This application is a continuation of U.S. application Ser. No. 12/692,438, filed Jan. 22, 2010, entitled, "Control System And Method for a Prosthetic Knee," which is a divisional of U.S. application Ser. No. 11/077,177, filed Mar. 9, 2005, entitled "Control System And Method for a Prosthetic Knee," which claims priority to U.S. Provisional Pat. App. No. 60/551,717, entitled "Control System And Method for a Prosthetic Knee," filed Mar. 10, 2004; U.S. Provisional Pat. App. No. 60/572,996, entitled "Control System And Method for a Prosthetic Knee," filed May 19, 2004; U.S. Provisional Pat. App. No. 60/569,511, entitled "Control System And Method for a Prosthetic Knee," filed on May 7, 2004; each of which is hereby incorporated by reference herein in its entirety.

This application also incorporates by reference U.S. Pat. No. 6,610,101, filed Mar. 29, 2001, issued Aug. 26, 2003; U.S. Pat. No. 6,764,520, filed Jan. 22, 2001, issued Jul. 20, 2004; U.S. Provisional Pat. App. No. 60/569,512, entitled "Magnetorheologically Actuated Prosthetic Knee," filed May 7, 2004; and U.S. Provisional Pat. App. No. 60/624,986, entitled "Magnetorheologically Actuated Prosthetic Knee," filed Nov. 3, 2004.

BACKGROUND

1. Field

The present invention relates to devices to be attached to limbs in general, such as prosthetics and orthotics, and, in addition, to an adaptive control method and system for an external knee prosthesis. Further, the present invention relates to a system and method of configuring and maintaining the adaptive control system for the external knee prosthesis.

2. Description of the Related Technology

Advances in microelectronics have enabled prosthetic systems, for example, prosthetic knees, to provide more natural functionality to patients who are equipped with such systems. However, the advances in electronics have thus far outpaced the advances in control systems. Thus, a need exists for improved control systems for prosthetic systems.

Moreover, the development of electronic control systems for prosthetic systems has created a need for systems and methods of configuring and monitoring the control systems. Many such systems have included special purpose hardware and custom user interfaces. Further, configuration options have typically been based on a prosthetist setting a variety of arbitrary damping parameters, in some cases, while the user walks on the knee. The custom controls and configurations make it more difficult and expensive to train prosthetists and prevent patients from being able to adjust their devices. Thus, a need exists for improved systems and methods of configuring and monitoring of the control systems of prosthetic systems.

SUMMARY

The system, method, and devices of the invention each have several aspects, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Embodiments" one will understand how the features of this invention provide advantages that include providing a prosthetic control system that provides more natural and comfortable movement to its users and enabling more convenient and intuitive configuration through graphical computing devices.

One embodiment is a device configured to be attached to a limb including a magneto-rheological (MR) damper. The device may be a prosthetic or orthotic. The MR damper may be configured to operate in shear mode. In one embodiment, the MR damper includes a rotary MR damper. A controller is configured to operate the damper. A mobile computing device may be adapted to intermittently communicate configuration parameters to the controller. The controller may also be adapted to intermittently communicate configuration parameters to the mobile computing device. The configuration parameters may include target values. In one embodiment, the controller is adapted to intermittently communicate operational data to the mobile computing device.

The mobile computing device may be a personal digital assistant. The personal digital assistant may be a commercial off-the-shelf unit. In other embodiments, the mobile computing device may be a mobile telephone handset, a personal computer, or a mobile personal computer. The mobile computing device may include a graphical user interface. The graphical user interface may display indicia associating parameter values with state machine conditions. The state machine conditions may include terrain conditions and/or gait cycle states. The graphical user interface may display indicia associating parameter values with adaptive parameters.

Another embodiment is a device configured to be attached to a limb including a controller configured to operate an actuator. The device may be a prosthetic or orthotic. A mobile computing device may have an iconic graphical user interface and adapted to intermittently communicate configuration parameters to the controller. The controller may be further configured to communicate data to the mobile computing device. The graphical user interface may display indicia associating parameter values with state machine conditions. The state machine conditions may include terrain conditions and/or gait cycle states. The graphical user interface may display indicia associating parameter values with adaptive parameters.

Yet another embodiment is a prosthetic or orthotic knee system that includes a MR damper. The MR damper may be configured to be operated in shear mode. The MR damper may include a rotary MR damper. A software system is configured to adaptively change damping parameters of the damper while the system is operating. A mobile computing device may be adapted to intermittently communicate damping parameters to the software system. The software system may be further configured to communicate data to the mobile computing device. The damping parameters may include target values.

Another embodiment is prosthetic or orthotic knee system including an MR damper. The MR damper may be configured to be operated in shear mode. The MR damper may include a rotary MR damper. A controller may be configured to operate the damper, wherein the controller is configured to receive data from a computing network. The computing network may include the Internet. A wireless transceiver may be configured to receive the data from the computing network. The data may be sent from a network computing device. The controller may also be configured to send data to the network. The data received from the computing network may be executable software. The controller may be configured to execute the executable software.

Another embodiment of a prosthetic or orthotic knee system may include a MR damper and a controller configured to operate the damper. The MR damper may be configured to be operated in shear mode. The MR damper may include a rotary MR damper. The controller is configured to send data to a computing network. The computing network may include the Internet. A wireless transceiver may be configured to send the data to the computing network. The data may be sent from a network computing device.

Another embodiment is a method of maintaining an electro-magnetic actuator in a prosthesis or orthotic that is actuated by a first current pulse having a first current polarity. The prosthesis may be an MR knee. The method may include applying a second current pulse to the electro-magnetic actuator wherein the current pulse has an electrical current polarity that is opposite the first current polarity. The second current pulse may have a magnitude that is determined with reference to a maximum current value. The maximum current value may be measured since the time of a third pulse having an electrical current polarity that is opposite the first current polarity. Preferably, the second current pulse has a magnitude that is in the range of one fifth to one half of the maximum current value. More preferably, the second current pulse has a magnitude that is in the range of one fourth to one third of the maximum current value. In one embodiment, the second current pulse has a magnitude that is approximately one fourth of the maximum current value.

Another embodiment is a method of controlling a prosthetic knee during swing extension while descending stairs. The prosthetic knee may be a MR knee. The method may include identifying a stair swing extension state, measuring an extension angle of the knee, and damping the identified swing of the knee with a first gain value only if the extension angle is less than a predetermined value and a second gain value otherwise. The second gain value may be substantially zero. The first gain value may be greater than the second gain value. The first gain value may be substantially greater than the second gain value. The predetermined value may include a soft damping angle. The step of identifying may include detecting the absence of a preswing. The step of detecting the absence of a preswing may include measuring a moment, and determining whether the moment is less than a weighted average of a plurality of measured moments. Measuring the moment may include measuring a knee angle rate, measuring a knee load, and calculating the moment from the knee angle rate and the knee load.

Yet another embodiment is a method of controlling a prosthetic knee system, including measuring at least one characteristic of knee movement, identifying a control state based at least partly on the at least one measured characteristic of knee movement, calculating a damping value based at least partly on the control state, and applying the damping value to control the resistance of a MR damper. The MR damper may be configured to operate in shear mode. The MR damper may include a rotary MR damper. The measuring may include receiving a value from a knee angle sensor and/or receiving a value from a load sensor. Receiving a value from the load sensor may include receiving at least one value from a strain gauge. In one embodiment the damping value is filtered based at least partly on values of previous damping values. The filtering may include applying a fixed point infinite impulse response filter to filter the damping value. The calculating may include adapting a damping parameter. The adapting may be based at least partly on an empirical function.

Another embodiment is a prosthetic knee system that includes a MR damper, at least one sensor configured to measure knee motion; and a software system configured to identify a control state based at least partly on the measure of knee motion and configured to send a control signal to the damper based at least partly the control state. The MR damper may be configured to operate in shear mode. In one embodiment, the MR damper includes a rotary MR damper. The at least one sensor may include a knee angle sensor, a load sensor, and/or at least one strain gauge. The control signal may include a current. The damper may be configured to vary resistance to rotation in response to the current. The software system may be further configured to filter a value of the control signal based at least partly on values of previous control signals. The software system may also be configured to apply a fixed point infinite impulse response filter to filter the value of the control signal.

Another embodiment is a method of controlling a prosthetic having a movement damper. The method may include measuring at least one characteristic of prosthetic movement, calculating a damping value based at least partly on the control state, applying a fixed point infinite impulse response filter to filter the damping value based at least partly on values of previous damping values, and applying the damping value to control the resistance of a damper.

Another embodiment is a method of controlling a device attached to a limb. The controlled device may be a prosthetic or orthotic. The method includes reading data from at least one sensor at a first frequency. A damping value is updated at a second frequency based on the data of the at least one sensor. The damping value is applied to an actuator at the first frequency. Preferably, the first frequency is greater than the second frequency.

Yet another embodiment is a method of controlling a device attached to a limb. The controlled device may be a prosthetic or orthotic. The method includes controlling at least one of a sensor and an actuator at a first frequency. Data associated with the at least one of the sensor and the actuator are processed at a second frequency. Preferably, the first frequency is greater than the second frequency.

Another embodiment is a prosthetic or orthotic system. The system includes a first module adapted to control at least one of a sensor and an actuator at a first frequency. A second module is adapted to process data associated with the at least one of the sensor and the actuator at a second frequency. Preferably, the first frequency is greater than the second frequency.

Another embodiment is a prosthetic or orthotic system. The system includes a means for controlling at least one of a sensor and an actuator at a first frequency and a means for processing data associated with the at least one of the sensor and the actuator at a second frequency. Preferably, the first frequency is greater than the second frequency.

Another embodiment is a computer-readable medium having stored thereon a computer program which, when executed by a computer, controls at least one of a sensor and an actuator at a first frequency and processes data associated with the at least one of the sensor and the actuator at a second frequency. Preferably, the first frequency is greater than the second frequency.

DETAILED DESCRIPTION

The following detailed description is directed to certain specific embodiments of the invention. However, the invention can be embodied in a multitude of different ways as defined and covered by the claims. In this description, reference is made to the drawings wherein like parts are designated with like numerals throughout.

It is to be appreciated that depending on the embodiment, the acts or events of any methods described herein can be performed in any sequence, may be added, merged, or left out all together (e.g., not all acts or events are necessary for the practice of the method), unless the text specifically and clearly states otherwise. Moreover, unless clearly stated otherwise, acts or events may be performed concurrently, e.g., through interrupt processing or multiple processors, rather than sequentially.

Further, for convenience and clarity of discussion, certain embodiments of systems and methods are described herein with respect to a prosthetic knee. However, it is to be appreciated that the principles discussed with respect to the exemplifying embodiments may also be applied to systems and methods directed to knee, ankle or foot or even other joints. Moreover, these principles also apply to orthotics, muscle replacement, or muscle assist devices as well as prosthetics.

The terms "prosthetic" and "prosthesis" as used herein are broad terms and are used in their ordinary sense and refer to, without limitation, any system, device or apparatus usable as an artificial substitute or support for a body part.

The terms "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

Figure 1:
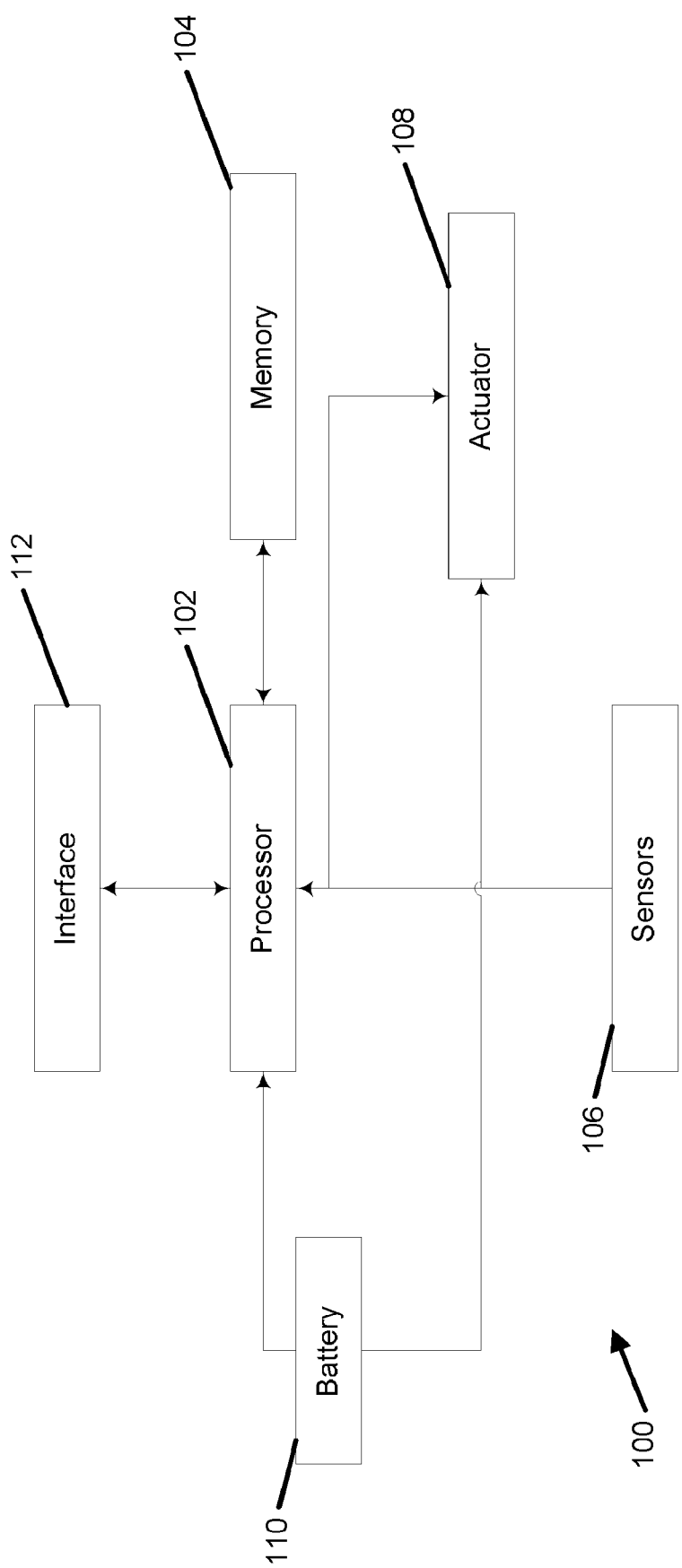
FIG. 1 is a simplified block diagram of one embodiment of a control system for a prosthetic device, such as a prosthetic knee.

FIG. 1 is a top level block diagram that depicts one embodiment of a prosthetic limb and a system for configuring and monitoring the prosthetic device. A prosthetic system 100 may include a prosthetic knee that includes a damper for controlling the amount of resistance that the knee produces at the joint. In a knee embodiment, the system 100 includes a magnetorheological (MR) damper and sensors that provide data measuring, e.g., knee angle, knee angle rate of change, and mechanical loading of the knee. More preferably, the knee system includes an MR damper operating in shear mode such as described in the above-incorporated U.S. Pat. No. 6,764,520, U.S. Application No. 60/569,512, and U.S. Application No. 60/624,986, i.e., a prosthetic knee joint that operates in shear mode, for example, where an MR fluid is provided between adjacent surfaces, such as between parallel plates or in the annular space between inner and outer cylinders. In this exemplifying embodiment, a control current is applied through an actuator coil to the MR fluid to modulate the resistance of the joint to rotary motion.

The prosthetic device 100, e.g., a prosthetic knee, may include a computer processor 102, attached to a memory 104. The processor may be any general or special purpose processor, such as, for example, a Motorola MC68HC912B32CFU8. The memory 104 may include volatile components, such as, for example, DRAM or SRAM. The memory 104 may also include non-volatile components, such as, for example, memory or disk based storage. The processor 102 may be coupled to one or more sensors 106 that provide data relating to, for example, the angular rate, position, or angle of the knee 100.

The processor 102 is coupled to one or more actuators 108. In one embodiment, the prosthetic device includes one or more movable joints, and each joint has one or more actuators 108. The actuators 108 of a joint may include a damper that is configured to control damping, e.g., the resistance to motion, of the joint. Damping generally refers to providing resistance to a torque, e.g. rotational motion or torque of a knee, foot, or other joint.

In one embodiment, maintenance of smooth and relatively natural movement with the prosthetic device 100 is achieved by frequent processing of data from the sensors 106 with correspondingly frequent updates of the control input to the actuator 108. Thus, a low-level sensor reading process may be configured to frequently provide generalized control of the actuator. A high-level process may concurrently operate at a lower speed to, for example, sense state changes, or adapt to the particular gait pattern of the user. In one preferred embodiment, the sensors 102 produce data with a frequency, or duty cycle, of at least approximately 1000 Hz that is used by a low-level, e.g., interrupt driven, software process on the processor 102 to maintain the damping for a given state. In this preferred embodiment, the processor 102 also executes a high-level process that updates the system state with a frequency, or duty cycle, of at least approximately 200 Hz. Control of the actuator 108 may occur in the low-level process at higher frequency, e.g., at the frequency of readings from the sensor 102. In one preferred embodiment, control of the actuator 108 is maintained at 1000 Hz. By maintaining low-level actuator control at a higher frequency than high-level state determination and motion adaptation, a lower power (for longer-battery life) and lower cost processor 102 can be employed. The low-level and high-level routines may communicate through inter-process communication (IPC) mechanisms that are well known in the art, e.g. through a shared block of memory or a shared data structure.

In one embodiment, a software system translates inputs from the sensors into current command for the actuator and monitors the health of the system providing user warning in failure modes. Ancillary functions may include communication with external devices implementation of user control functions, recording of key performance parameters, diagnostic and test functions, and parameter recording during debug mode.

In one embodiment, the software is logically decomposed into the low-level and high-level routines, or modules, discussed herein. Lower level or operating system code may provide basic functionality and support for the operation of the knee. High-level code makes decisions at a higher level concerning the operation of the prosthetic and implements these decisions through interfaces provided by the low-level code. In particular, in one exemplifying embodiment, the low-level code include hardware initialization, scheduling, communication, high-level code loading, low-level debug and test, data recording, virtual damper implementation. In this embodiment, the high-level routines include high-level initialization, parameter read routing, a main operational routine, state machine operation, damping parameter level and mode determination, auto adaptation settings, safety, parameter set routine, user control functions, storage of user specific data. Interface between the low-level and high-level routines may occur through a series of function calls. In the exemplifying embodiment, the high-level routines provides interfaces for use by the low-level routines that include initialization functions, parameter reading function, the main operating function, and an output control function. Additional specialized functions interfaces include calibration, parameter storage, and PDA interface functions. Other interface between the high-level and the low-level routines include virtual damper control functions and debug support.

In an exemplifying embodiment, when power is supplied to the system, the low-level code begins operation and initializes the hardware system. The low-level routines checks for the presence of stored high-level routines. If the high-level routines are present, the high-level routines are loaded into memory and started. If not, the low-level code opens the communications channel and waits for external instructions. If the high-level routines are present, load successfully and pass a check sum validation, the low-level routines first call an initialization routine presented by the high-level routines. After this completes, the low-level routines begin the scheduling system. The scheduler executes low-level routines every 1 ms and high-level routines every 5 ms. At the beginning of each 5 ms loop, the low-level routines first determine if the high-level code has completed its last cycle. If not, scheduling is deferred until the next 1 ms time slot. If the high-level routines did complete the last cycle, the high-level routines for the parameter read function, main operating function and output control function are executed. This cycle continues until power down or unless interrupted by receipt of communication from an instrumentation system or from another computing device, such as described below.

In a preferred embodiment, the low-level code is firmware and the high level code is usercode. The modules of the firmware sub-system include communications, data recording, debug routines, global variables, interrupt service vectors, scheduler, serial communications routines, initialization routines, shared communication data, serial peripheral interface control routines, timer control routines, version information, warning control routines, a/d control, damping control routines, and assembly language start system. The usercode sub-system includes global variables, instrumentation variables, non-volatile storage management, main control routines, system health monitor, sensor and actuator control, and shared communications data.

It is to be appreciated that each of the modules comprises various sub-routines, procedures, definitional statements and macros. Each of the modules may be separately compiled and linked into a single executable program. The following description of each of the modules is used for convenience to describe the functionality of one embodiment of a system. Thus, the processes that are performed by each of the modules may be redistributed to one of the other modules, combined together in a single module, or made available in, for example, a shareable dynamic link library. The modules may be produced using any computer language or environment, including general-purpose languages such as C, Java, C++, or FORTRAN.

In the preferred embodiment, a global variable module is configured to instantiate variables. The system 100 maintains a large structure that is a global array of floating point values. This structure serves several purposes. First, it allows a centralized storage area for most variables used in the usercode and some variables used in firmware. Second, it allows access to those variables by routines in the data module so that they can be recorded and accessed without intervention of the usercode.

In the exemplifying embodiment, the global data structure may include three data arrays. The first is a global array of floating point variables. If the instrumentation system is to be configured to report a variable it is placed in this array. The second array is an array of structures that provide information about variables that are contained in the global array and are therefore eligible for recording and reporting. It is not necessary to include references to each variable in the global array in the second array but only to those variables accessed by the instrumentation system. The information in this array of structures is used by the data module to manage the recording of and transmission of information. The third array is identical to the second array but manages variables sent to the PDA when it is connected. This is generally a subset of the variables available for transmission to the instrumentation system.

By separating the functions of high-level adaptation and/or gait related calculations from the low-level control functions, the software of the high-level process may be updated or replaced independently of the low-level control software. Advantageously, this division of the software also encapsulates different hardware embodiments and the corresponding low-level software from the high-level functionality. Thus, control programs related to, for example, a specific activity may be used without needing to be customized or configured for a given embodiment of the hardware.

A battery 110 and associated power control and switching electronics (not shown) may be coupled to each of the processor 102, the memory 104, the sensors 106, and the actuator 108. The battery 110 may also include a charging circuit, or include a connector for coupling the battery 110 to a charging circuit.

While embodiments of prosthetic devices are discussed herein with respect to embodiments of prosthetic knees, the prosthetic device 100 may also be embodied in prosthetic devices other than knees, such as prosthetic feet and ankles, for example as described in U.S. application Ser. No. 11/056,344, filed Feb. 11, 2005, the entirety of which is hereby incorporated by reference. It will be appreciated that the concepts described above can be incorporated into orthotic devices as well.

The processor 102 of the system 100 may also be coupled to an interface 112. The interface 112 may include a serial port, a Universal Serial Bus (USB), a parallel port, a Bluetooth transceiver and/or any other communications port. In particular, the interface 112 may also comprise a network interface. The interface 112 may provide network connectivity to including, for example, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), Bluetooth (IEEE 802.15.1), or infrared interfaces including IRDA. Note that computing devices may be desktop, server, portable, handheld, set-top, or any other desired type of configuration. As used herein, the network includes network variations such as the public Internet, a private network within the Internet, a secure network within the Internet, a private network, a public network, a value-added network, an intranet, and the like.

In various embodiments, the processor 102, memory 104, sensors 106, and the interface 112 may comprise one or more integrated circuits with each of these components divided in any way between those circuits. In addition, components may also comprise discrete electronic components rather than integrated circuits, or a combination of both discrete components and integrated circuits. More generally, it is to be appreciated that while each element of the block diagrams included herein may be, for convenience, discussed as a separate element, various embodiments may include the described features in merged, separated, or otherwise rearranged as discrete electronic components, integrated circuits, or other digital or analog circuits. Further, while certain embodiments are discussed with respect to a particular partitioning of functionality between software and hardware components, various embodiments may incorporate the features described herein in any combination of software, hardware, or firmware.

In operation, the processor 102 receives data from the sensors 106. Based on configuration parameters and the sensor data, adaptive control software on the processor 102 sends a control signal to the knee actuator 108. In one embodiment, the knee actuator 108 is a magnetorheological (MR) brake. The brake may be of the class of variable torque rotary devices. The MR actuator 108 provides a movement-resistive torque that is proportional to an applied current and to the rate of movement. The control signal may drive a pulse width modulator that controls current through a coil of the actuator 108 and thus controls the magnitude of the resistive torque.

Figure 2:
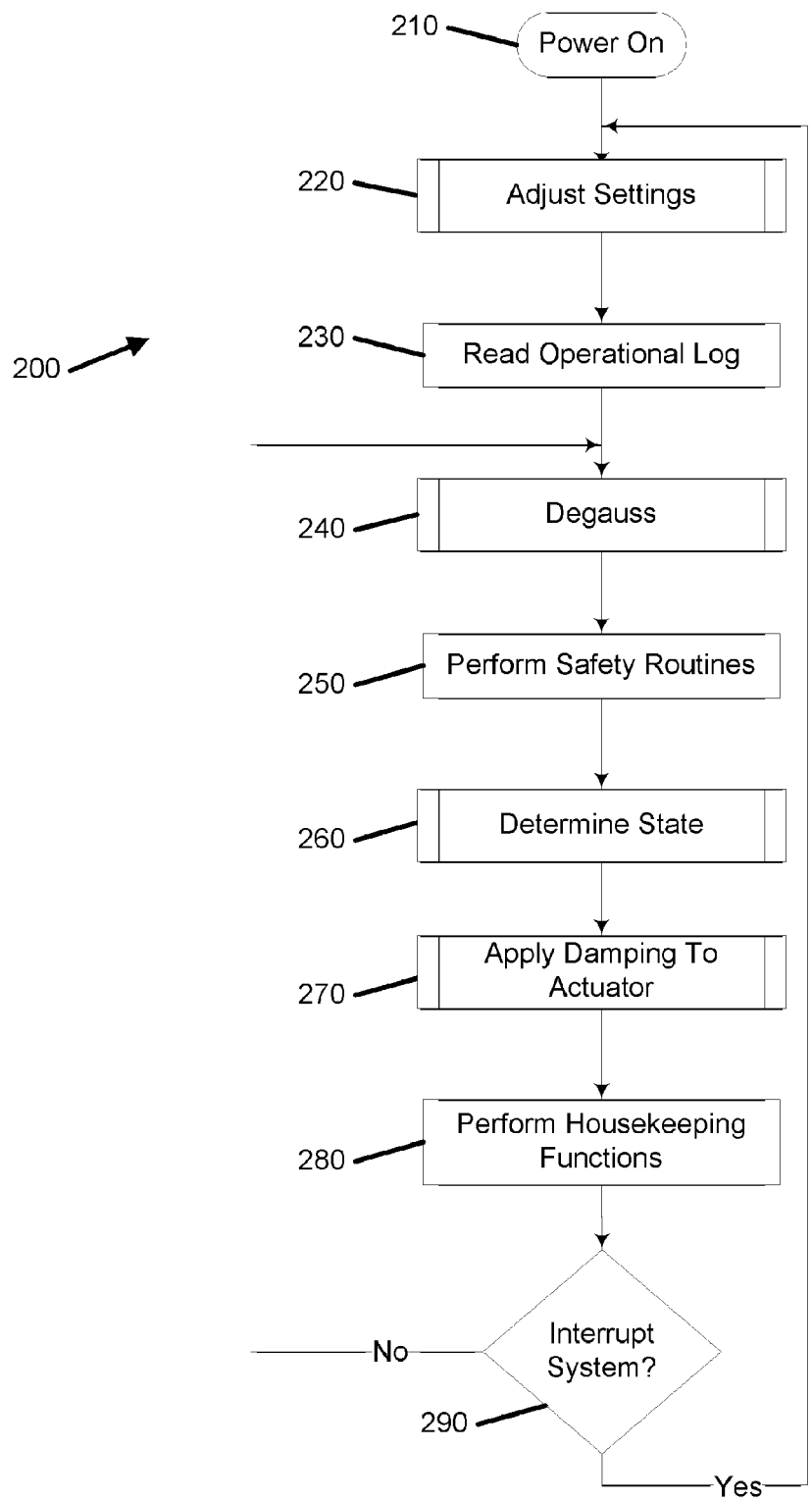
FIG. 2 is a top level flowchart depicting one embodiment of a method of controlling a knee using a control system such as depicted in FIG. 1.

FIG. 2 is a flowchart depicting one embodiment of a method 200 for controlling a prosthetic device, such as a prosthetic knee 100. It is to be appreciated that depending on the embodiment, additional steps may be added, others removed, steps merged, or the order of the steps rearranged. In other embodiments, certain steps may performed concurrently, e.g., through interrupt processing, rather than sequentially. The method 200 begins at step 210 in which the device 100 is powered on. Moving on to step 220, the settings or control parameters for the prosthetic 100 may be adjusted, e.g., after the initial power on for a new prosthetic 100. This step 220 is discussed in more detail, below, with reference to FIG. 4. Continuing at step 230, the processor 102 may read an operational log. For example, if the processor 102 detects a previous crash or other operational abnormality in the log, it may perform additional diagnostic routines. In one embodiment, the processor may communicate portions of the log via interface 112 to, e.g., a service center.

Next at step 240, the method 200 begins the main control sequence. At step 240, the system 100 may degauss the actuator 240. For example, in an MR damper, the application of the control current to the actuator may cause a residual magnetic field to be imparted to the steel plates that make up the actuator. This can cause a degradation in the performance of the actuator. Advantageously, the application of a current pulse having the opposite polarity of the current pulses used for damping can degauss the actuator, i.e., remove the residual magnetization. Step 240 is discussed in more detail below with reference to FIG. 10.

Continuing at step 250, the system 100 may perform safety routines. Safety routines may include detecting, for example, whether the user of the knee 100 is losing balance and hold the knee in a locked upright position to prevent the user from falling. Moving to step 260, the method 200 determines the state of the system 100. In one embodiment, the state may correspond to a physical or kinesthetic state of the prosthetic. Preferably, the state in a knee embodiment of system 100 is related to a state in a human gait cycle. Step 260 is discussed below in more detail with reference to FIGS. 8 and 9. Moving to step 270, the method 200 includes applying a damping value to the actuator 108. Step 270 is also discussed in more detail below with reference to FIG. 7.

Continuing at step 280, housekeeping functions may be performed. In one embodiment, this may include the processor 102 reading values from the sensors 106, e.g., during interrupt handling routines. Housekeeping functions may also include activity related to maintaining the battery 110, e.g., battery conditioning, checking charge levels, or indicating to the user that the battery 110 is, e.g., at a specified discharge level. Next at step 290, the system 100 checks for an interrupt to the system, e.g., a command to enter the adjustment mode. If the system is interrupted, the method 200 returns to step 220. If the system is not interrupted, the method 200 continues at step 240. In one embodiment, the step 270 may be performed in a low-level process that operates at a higher frequency than, for example, the determination of the state at step 260 running in a high-level process.

Figure 3:
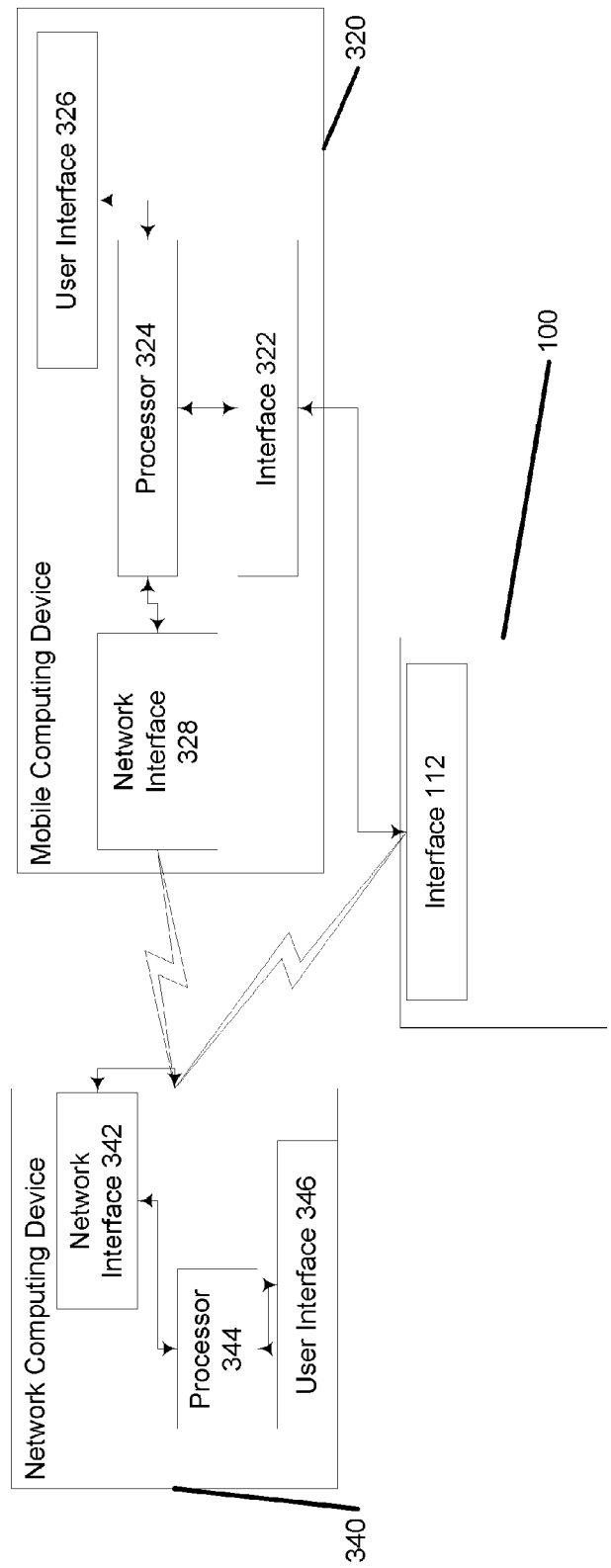
FIG. 3 is diagram conceptually depicting embodiments of a system for remote configuration and monitoring of a control system of a prosthetic knee such as depicted in FIG. 1.
Figure 3A:
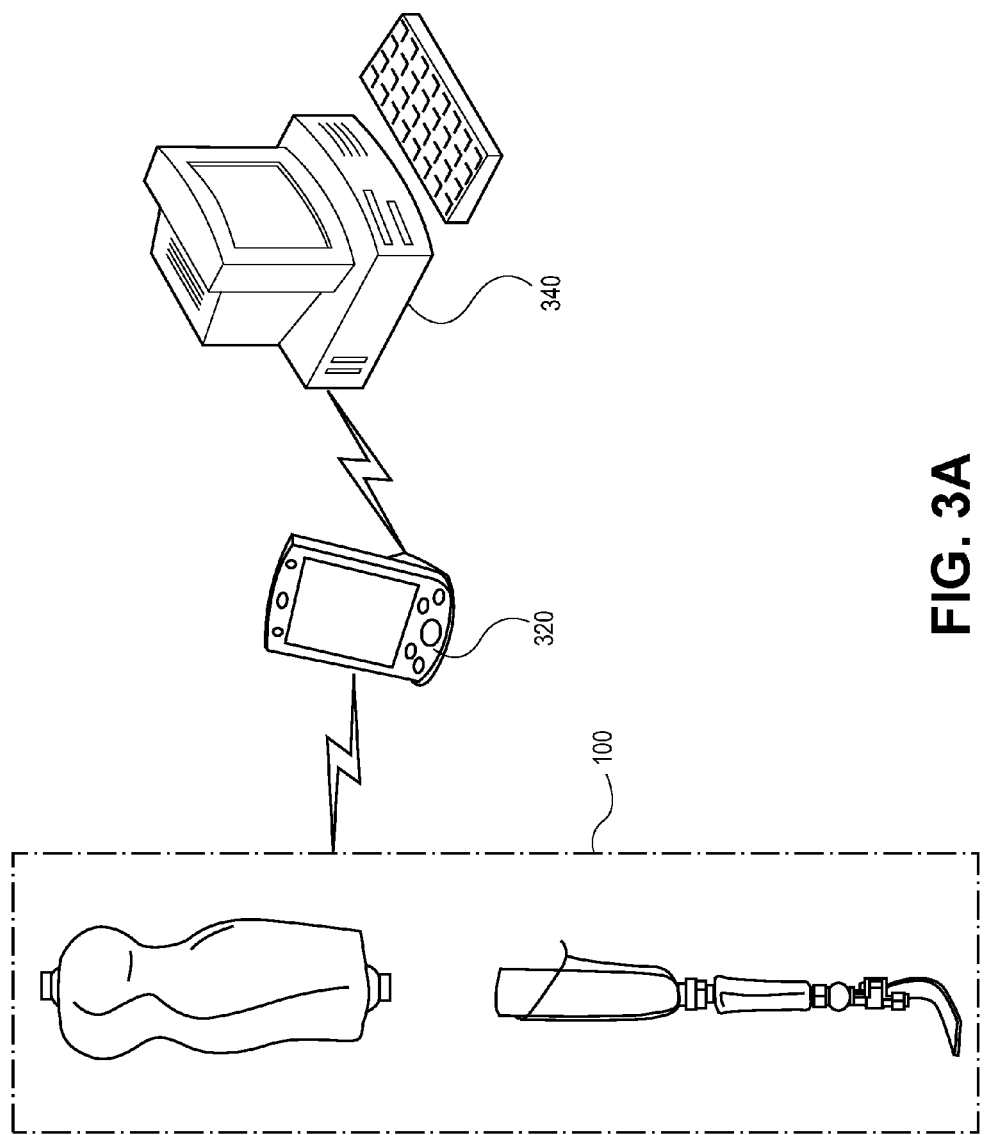
FIG. 3A is a diagram conceptually depicting one embodiment of the system of FIG. 3 that includes a prosthetic knee system.

As depicted in FIG. 3, the system 100 may be in digital communication with a mobile computing device 320. The term "mobile" in the context of a computing device generally refers to any computing device that is configured to be readily transported. Such devices generally, but not necessarily, are configured to receive power from a battery. For example, mobile computing devices may be a personal data assistant (PDA), a mobile telephone handset, a laptop computer, or any other general or special purpose mobile computing device. In various embodiments, the mobile computing device 320 operates using a standard mobile operating system, such as, for example, Microsoft PocketPC, or PalmOS. Furthermore, the mobile computing device may be a commercial-off-the-shelf (COTS) unit. Generally, the mobile computing device 320 includes an interface 322 that is compatible with the interface 112. A processor 324 is coupled to the interface 322 and executes software that provides a user interface 326. In one embodiment, the interface 326 is a graphical user interface including a bit-mapped display, such as, for example, a liquid crystal display (LCD). The mobile computing device 320 may also include a network interface 328. The network interface 328 may be in communication with a network computing device 340, e.g., a desktop, laptop, or server computer. FIG. 3A is a diagram conceptually depicting one embodiment of the system of FIG. 3 that includes a prosthetic knee 100, a PDA 320, and a desktop computer 340.

The network computing device may include a network interface 342 coupled to a processor 344 and a user interface 346. In one embodiment, the network interface 342 may also communicate with the network interface 112 of the prosthetic system 100.

In one embodiment, the mobile computing device 320 may provide a user interface for configuring operational parameters of the system 100. In particular, the user interface 326 may include one or more displays for configuring and monitoring of the knee 100. The configuration of the prosthetic system 100 is discussed below in more detail with respect to FIG. 4.

In addition to configuring the knee 100, the mobile computing device 320 may also be configured to receive performance and diagnostic information from the knee 100. For example, the prosthetic system 100 may send, via interfaces 112 and 122, data such as, for example, a total of the number of steps taken on a particular knee system 100, to the mobile computing device 320 for display via the user interface 126. Further, if the control system detects specific types of failures, these failures may be included in the data. In one embodiment, the user interface 126 may depict the number of times that a particular class of error has occurred.

In addition to configuration and maintenance through the mobile computing device 320, in one embodiment, a network computing device 140 may be adapted to configure and receive maintenance data from the knee 100 directly. In this case, the knee 100 may have a wireless transceiver integrated in it to handle computer network connectivity functions. In another embodiment, the network computing device 140 may be adapted to configure and receive maintenance data from the knee via the mobile computing device 320. FIG. 3 depicts a variety of different embodiments for providing configuration and maintenance access to a knee 100.

In various embodiments, a short distance protocol such as RS232, Bluetooth, or WiFi and an Internet connected device such as a programmable mobile telephone handset, a PC, laptop, PDA, etc., communicate remotely with a prosthetic device using the Internet or other suitable data network as the long distance transport media.

The software program running on processor 102 of knee or other prosthetic device 100 may be as simple as a double sided transponder or transceiver that creates a bridge between the interface 112 through the interfaces 322 and 328 on the mobile computing device 320 to an interface 342 on the network computing device 340 via, e.g., the Internet. The communication protocol used from the internet connected device to the service center end of the system may be any of a variety of suitable network protocols. Embodiments may use connection-oriented protocols such as TCP, or a combination of connection oriented protocols and connectionless packet protocols such as IP. Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure. The program may be a web service running on a PC that sends out a message to the service center each time the prosthetic device is connected and needs service.

In one embodiment, the prosthetic device 100 is directly coupled to a network, and thus to the network computing device 340. For example, interface 112 may be a WiFi (e.g., 802.11a, 802.11b, 802.11g) interface that connects to a network through a LAN or at public hotspots to transmit and receive data to either of the network computing device 340, or mobile computing device 320.

The network connection between the device 100 and the network computing device 340 (which may be via the mobile computing device 320) may use any appropriate application level protocol including, for example, HTTP, CORBA, COM, RPC, FTP, SMTP, POP3, or Telnet.

Figure 4:
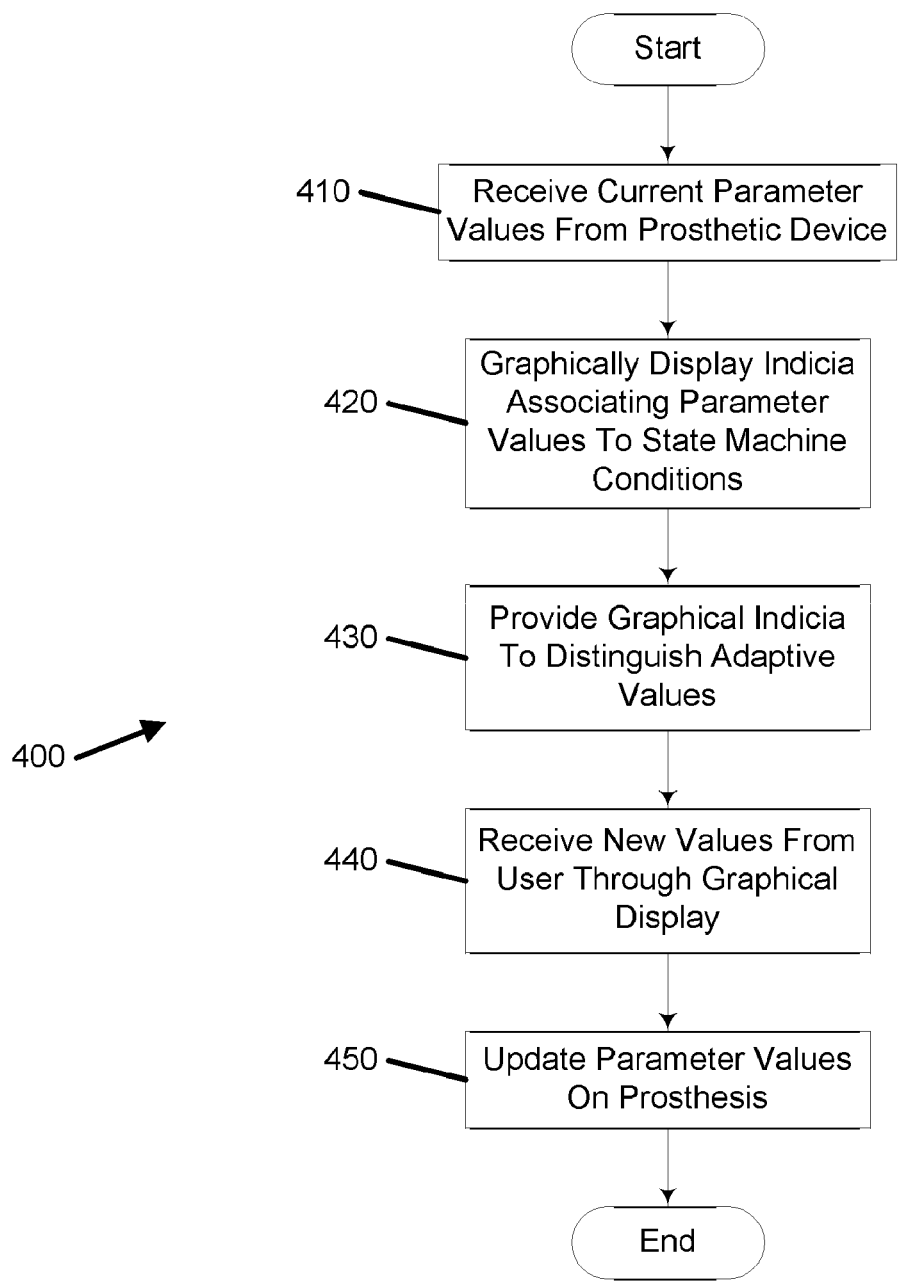
FIG. 4 is a flowchart depicting one embodiment of a method for configuring the control system of using embodiments of a system such as depicted in FIG. 4.

FIG. 4 is a flowchart depicting one embodiment of a method 400 for configuring the operational parameters of a prosthetic device 100. While an embodiment of the configuration method 400 will be discussed with respect to a knee embodiment of the device 100, it is to be appreciated that other embodiments of the method 400 can also be used to configure of other prosthetic or orthotic devices 100.

The method 400 proceeds from a start state to state 410 where, for example, the mobile computing device 320 receives a current parameter value from the prosthetic device 100. In one embodiment, the parameters may be target values, such as, e.g., the target flexion angle, transmitted through the interface 112. Next at step 420, the values of parameters may be displayed on a graphical user interface, e.g., user interface 326 of mobile computing device 320. The graphical user interface may associate graphical indicia relating to state machine conditions to the parameter values.

Figure 5:
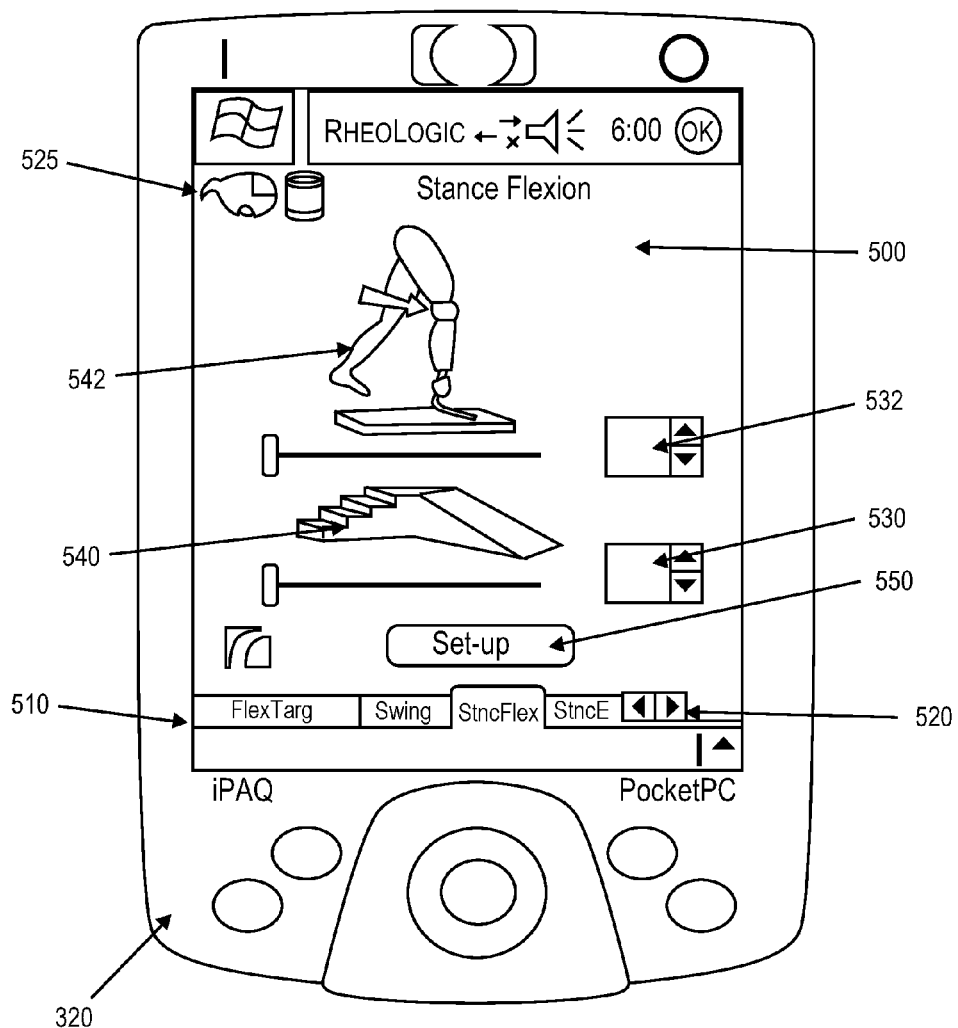
FIG. 5 is a screen shot depicting one embodiment of a graphical user interface for configuring a control system such as depicted in FIG. 1.

FIG. 5 is a screen display of one embodiment of a user interface display 500 for configuring settings of a knee embodiment of the prosthetic system 100. A notebook control 510 may be provided to select among different screens of parameters, with each screen allowing configuration of one or more parameters. This notebook control 510 may include a scroller 520 to enable scrolling through additional sets of values. The display 500 may include additional informational icons 525 to depict information such as the battery charge level of the system 100. In the exemplifying display 500 of FIG. 5, two parameters are shown for configuration on the same screen using data entry controls 530 and 532. Each parameter is associated with graphical indicia 540 and 542 which associate each value to be entered to a different state machine condition, e.g., stair or incline travel to parameter 530 by indicium 540 and flat terrain travel to indicium 542.

Continuing to step 430 of the method 400, the display may provide graphical indicia to distinguish adaptive values. In one embodiment, an adaptation configuration control 550 may be provided on the display 500 of FIG. 5. The control 550 may be displayed in a different color to indicate whether or not auto-adaptation is enabled. In one embodiment, when auto-adaptation of the configuration is enabled by control 550, the system 100 auto adapts the configuration parameters for, e.g., a knee being configured for a new user. This adaptation is described in more detail in the above-incorporated U.S. Pat. No. 6,610,101. This auto-adaptation is indicated by the control 550 being displayed in one color, e.g., blue. When the system 100 is not in auto-adaptation mode, e.g., after initial training of the system 100, the control indicates this by being displayed in a second color, e.g., gray.

Next at step 440 new values for parameters may be received from the user through the display 500. Moving to step 450, these new values are updated on the prosthesis system 100 by, e.g., communicating the values from the mobile computing device 320 through the interfaces 322 and 112, to the prosthetic system 100 and the method 400 ends.

Figure 6:
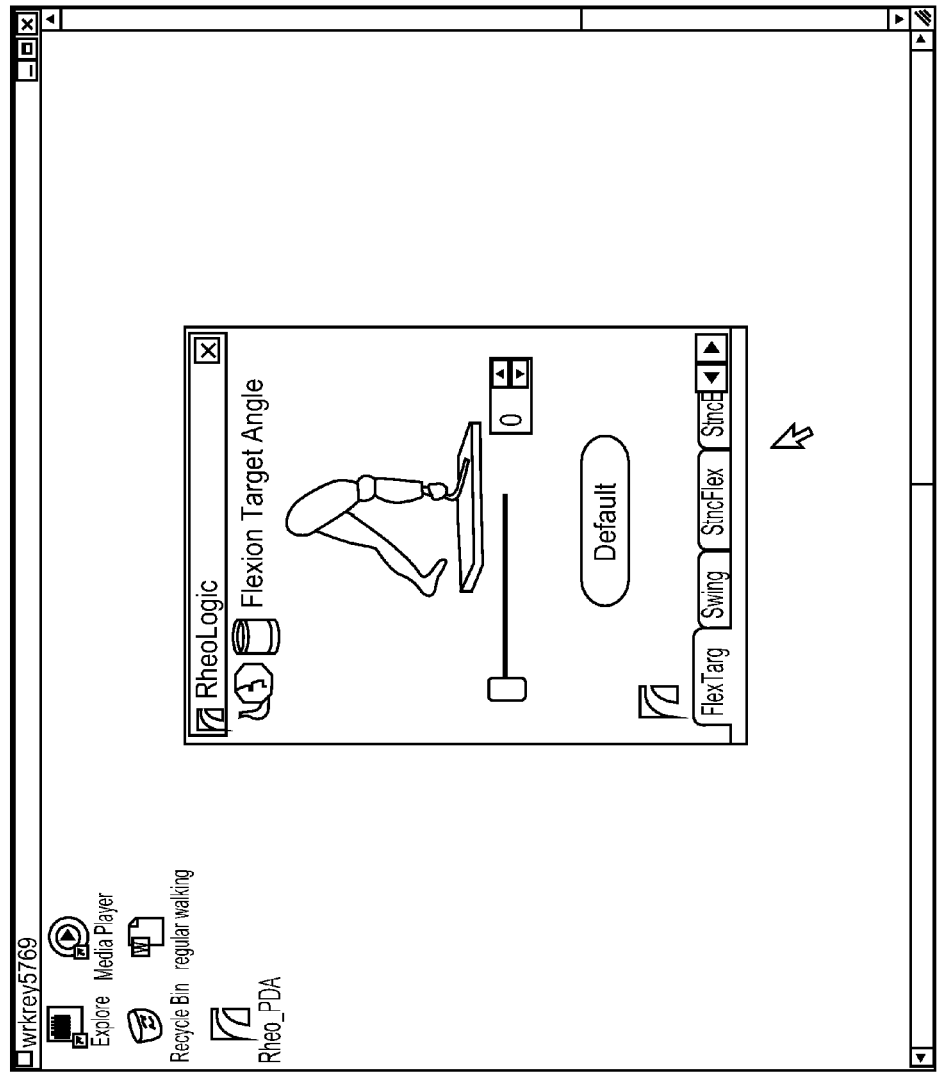
FIG. 6 is a screen shot depicting another embodiment of a graphical user interface configuring a control system such as depicted in FIG. 4.

FIG. 6 depicts a screen shot from one embodiment of a networked prosthetic configuration and monitoring system. In one embodiment, a knee 100 may be accessed via a virtual network computer (VNC) running on the mobile computing device 320 which is displayed and manipulated via the user interface 146 of network computing device 340. In this embodiment, the knee 100 uses a short distance protocol (RS232) and a 3 wire cable to connect the interface 112 of the knee 100 to the mobile computing device 320 which in this case is a personal computing, which may, for example, run a program that is a GUI that controls some of the settings of the knee 100.

A remote service person is able to open a remote screen on the network computing device 340 using the VNC program which represents the interface 326 of the mobile computing device 320 on the interface 346 the network computing device 340 for the service person is using on the other side of the Internet. In one embodiment, this connection enables remote debugging and maintenance of the knee 100 over the Internet, and thus from anywhere in the world. The network computing device 340 may access a configuration program for the prosthetic system 100 or it may access a diagnostic program capable of providing more detailed information and greater control over the device 100.

Embodiments of prosthetic device 100 may allow some or all of the following functions: remote or telemaintenance, remote prosthetic configuration, installation of software upgrades on the prosthetic system 100, collection of medical data, collection of activity data relating to the patient's use of the prosthetic system 100, and remote optimization of the system 100.

The software upgrade mechanism of the system may, for example, be automatic so the device 100 is up to date with the newest (and safest) version of the software directly from the network computing device 340. Software upgrades may include software to replace software that is already installed on the device 100, or software to add new features or capabilities to the device 100. In other embodiments, software upgrades may be downloaded from the mobile computing device 320. Such updates may be automatically, and/or manually initiated. Furthermore, software upgrades may be made to the mobile computing device 320 via the network computing device 340.

In one embodiment, users of prosthetic systems 100 may maintain a personal profile with a service center that includes the network computing device 340 and update the database with data on regular basis.

Figure 7:
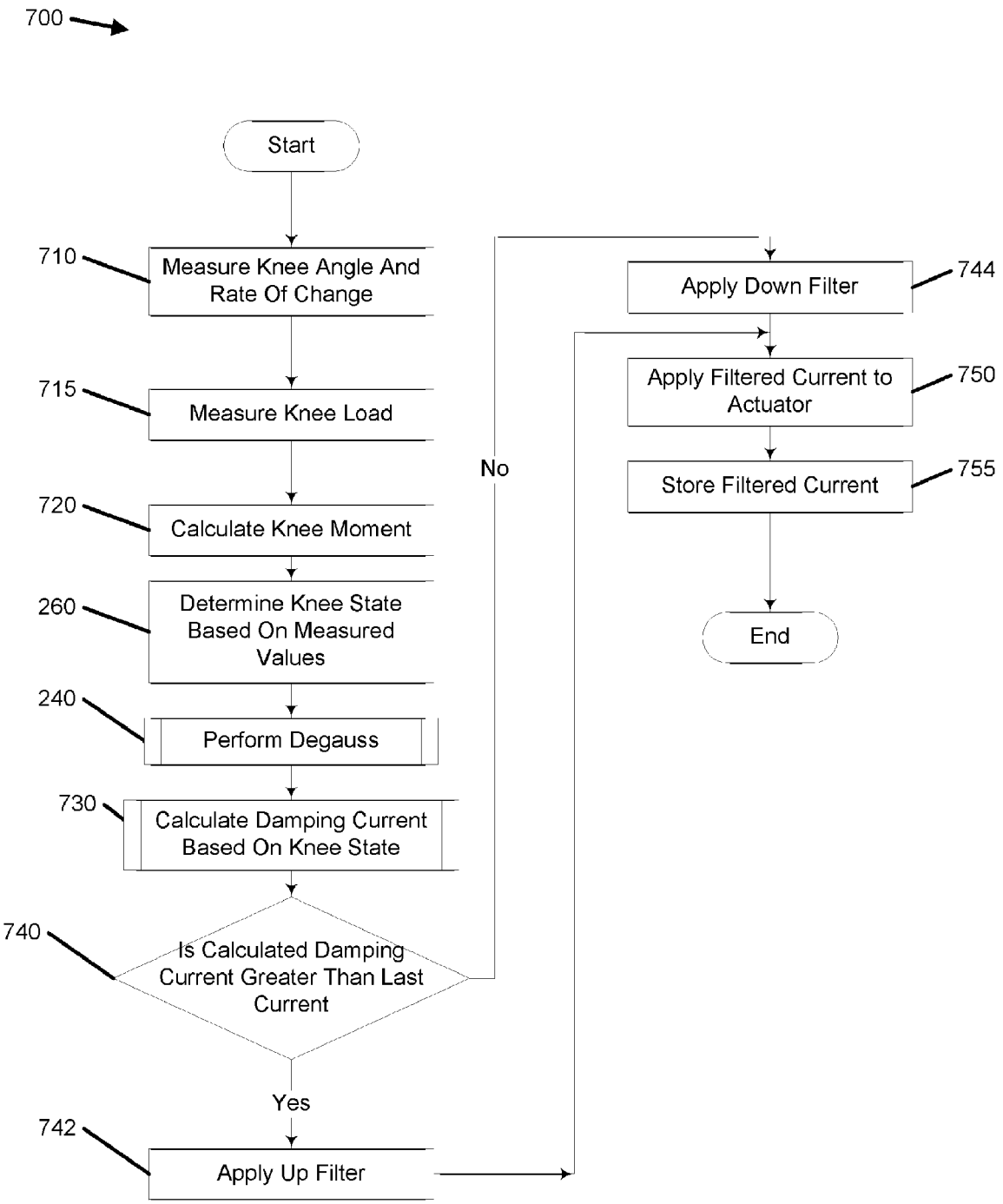
FIG. 7 is a flowchart depicting, in more detail, one embodiment of the method depicted of FIG. 2.

FIG. 7 is a flowchart depicting one embodiment of a method 700 for controlling the damping applied to the actuator 108 by the prosthetic system 100. The method 700 starts at step 710 where the knee angle and angular rate of change are measured by sensors 106. Next at step 715, the knee load is measured by the sensors 106. In one embodiment, this load measurement is calculated based on strain gauge sensor readings. Next at step 720, a knee moment is calculated. In one embodiment this is a difference between front and rear strain gauge counts.

Moving to a step 260, the knee state is determined based on the measured values. This determination is discussed in more detail below with reference to FIGS. 8 and 9. Next at step 240, degaussing of the actuator 108 may be performed. The degaussing process is discussed in more detail with reference to FIG. 10 below.

Moving to step 730, a damping current is calculated based on the knee state. Table 1 recites the formulas used to calculate the current in one embodiment of a MR knee system 100. These formulas employ constant values that are derived from the weight of a given device, user configuration, and constants based on the specific sensors and geometry of the system 100. The damping during swing flexion is based on a preconfigured target angle. Preferably, the default target angle is 60°.

TABLE 1

Damping Formulas by State in One Embodiment

| State | Formula |
|---|---|
| Stance Flexion 810 | angular rate * a configured parameter |
| Stance Extension 820 | angular rate * a configured parameter |
| Swing Extension 840 (At measured angles less than a specified soft impact angle) | 1 + (Angle − Soft_Impact_Angle) * Soft_Impact_Gain/SoftImpactAngle. |
| Swing Extension 840 (At measured angles greater than the specified soft impact angle) | angular rate * a configured parameter |
| Swing Extension 840 (Stairs, greater than Soft Impact Angle) | No Damping |
| Swing Flexion 840 (Measured angle greater a specified starting angle) | angular rate * (Angle − Start_Angle)/ Target_Angle |
| Swing Flexion 850 (Measured angle less a specified starting angle) | No Damping. |

Beginning at step 740, a filter is applied to the calculated damping current. At decision step 240, the current is compared to the last applied damping current. If the new value is greater than the last value, the method 700 proceeds to step 742. If the value is less than the last value, the method 700 proceeds to step 744.

Continuing at step 742, an up filter is applied to smooth the damping values to, for example, accommodate jitter or noise in the measurements from the 106. In one embodiment the filter is an infinite impulse response filter. The filter receives as input the computed current C, the value of the previous damping control cycle $O_{N-1}$, and a filter coefficient F. The output $O_N = F*C + (1-F)*O_{N-1}$. In one embodiment, this calculation is performed using fixed point mathematics to enable faster processing. In one embodiment, the fixed point numbers are represented in 8 bits allowing 245 levels of filtering. Next, the method 200 moves to the step 750. Returning to step 744, a down filter is applied as in step 742 with the exception of the filter value being different. Using different filtering coefficients for up and down filtering enables greater control over the filtering and, e.g., enables increases in the magnitude of damping to be faster or slower than decreases in the magnitude of damping.

Next at step 750, the filtered current value is applied to the actuator 108. Finally at step 755, the applied filtered current value is stored for use in later invocations of the method 700.

Returning to step 260 of FIG. 7, in one embodiment of the method 700, the knee state is determined based on measured sensor values along with the current state. In one embodiment of the system 100, the processor may determine whether to change state or remain in the existing state at frequent intervals. Preferably, these intervals are no more than 5 ms. Some state transitions may not be allowed in a particular embodiment.

It is to be appreciated that, in some embodiments, the acts and events related to the steps depicted in FIG. 7 may be performed in different processes. For example, a low-level, hardware specific process may perform steps related to reading the sensors 102, such as in steps 710 and 715, and steps related to applying the current to the actuator such as in step 750 while a high-level process performs the steps related to determining state and calculating new damping current values, such as at step 260 and 730, 740, 742, or 744. In one embodiment, the low-level process performs the acts related to the associated steps at one frequency while the high-level process performs the acts related to the respective associated steps at a second frequency. Preferably, the first frequency is greater than the second frequency. More preferably, the first frequency is 1000 Hz and the second frequency is 200 Hz.

Figure 8:
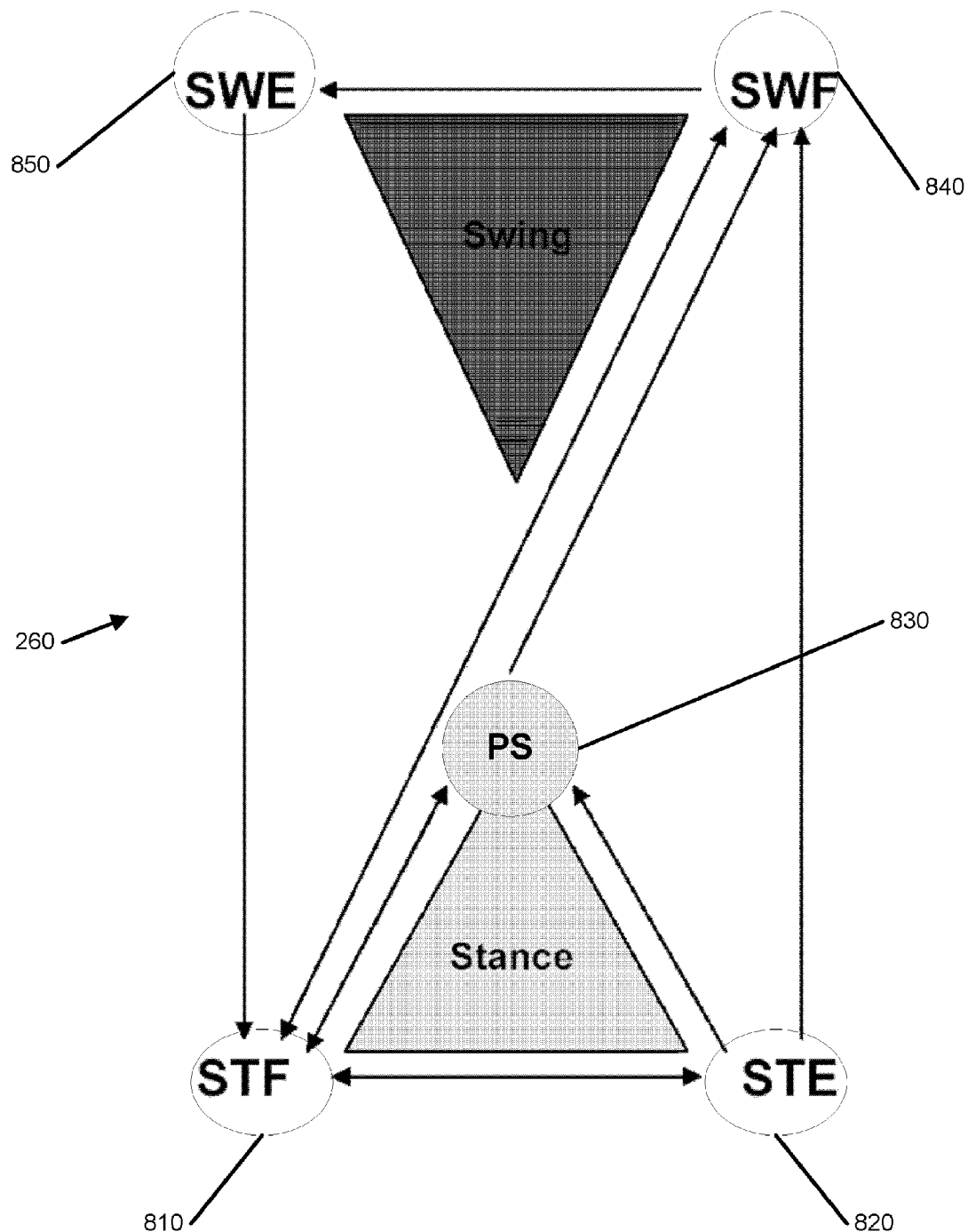
FIG. 8 is a conceptual state diagram depicting the states and transitions in a gait cycle of a control system such as depicted in FIG. 1.

FIG. 8 is a state diagram depicting a conceptual model of a human gait cycle that corresponds to the state machine of one embodiment of the method 200 directed to a prosthetic knee. State 810 is a stance flexion state (STF). This represents a state of the knee from initial contact with the ground through the continued loading response of the knee. The user may flex or extend the knee to some degree while in this state. The knee remains in this state so long as the knee has not begun extending. Simple, e.g., mechanical, embodiments of a knee prosthetic typically do not support the standing flexion of the knee represented by this state. Preferably, the knee system 100 recognizes this state and allows standing flexion to enable a more natural gait for users.

State 820 is a stance extension state (STE). This state represents gait positions where the knee moves from flexion to full extension. Patients who have developed a characteristic gait while using less advanced prosthetics may not encounter this state.

State 830 is a pre-swing state (PS). This state represents a transition state between stance and swing. During this state, in one embodiment of the method 200, the knee torque may drop to a minimum value in order to allow for easy initiation of knee flexion. In normal walking, this occurs during the time that the knee destabilizes in pre-swing to allow initiation of knee flexion while the foot remains on the ground.

State 840 is a swing flexion state (SWF). This state represents the swing phase of the lower leg in a human gait. A typical value for the angle of knee flexion is 60°. State 850 is a swing extension state (SWE). This state represents the gate phase in which the knee begins to extend.

Normal level ground walking typically consists of one of the following two state patterns. This pattern includes a state transition pattern of the STF state 810, to the STE state 820, to the PS state 830, to the SWF state 840 and finally to the SWE state 850. This pattern follows a gait pattern more closely resembling nominal human walking. However, this pattern may be less common among amputees and thus requires more practice to consistently use this feature. Advantageously, by recognizing each of the states 810, 820, 830, 840, and 850, the knee prosthetic system 100 may support this pattern by maintaining knee stability following initial knee flexion in early stance. Once patients learn to trust the resulting stance control of the knee prosthetic system 100, this gait pattern may be utilized.

As noted above, long term amputees accustomed to less advanced prosthetics may develop a second characteristic walking pattern. This pattern includes a state transition pattern of the STF state 810, to the PS state 830, to the SWF state 840 and finally to the SWE state 850. The stance extension state is thus skipped because the prosthesis remains extended from initial contact until pre-swing. Although this is a deviation from normal human locomotion, this is a typical gait pattern for a transfemoral amputee.

Figure 9:
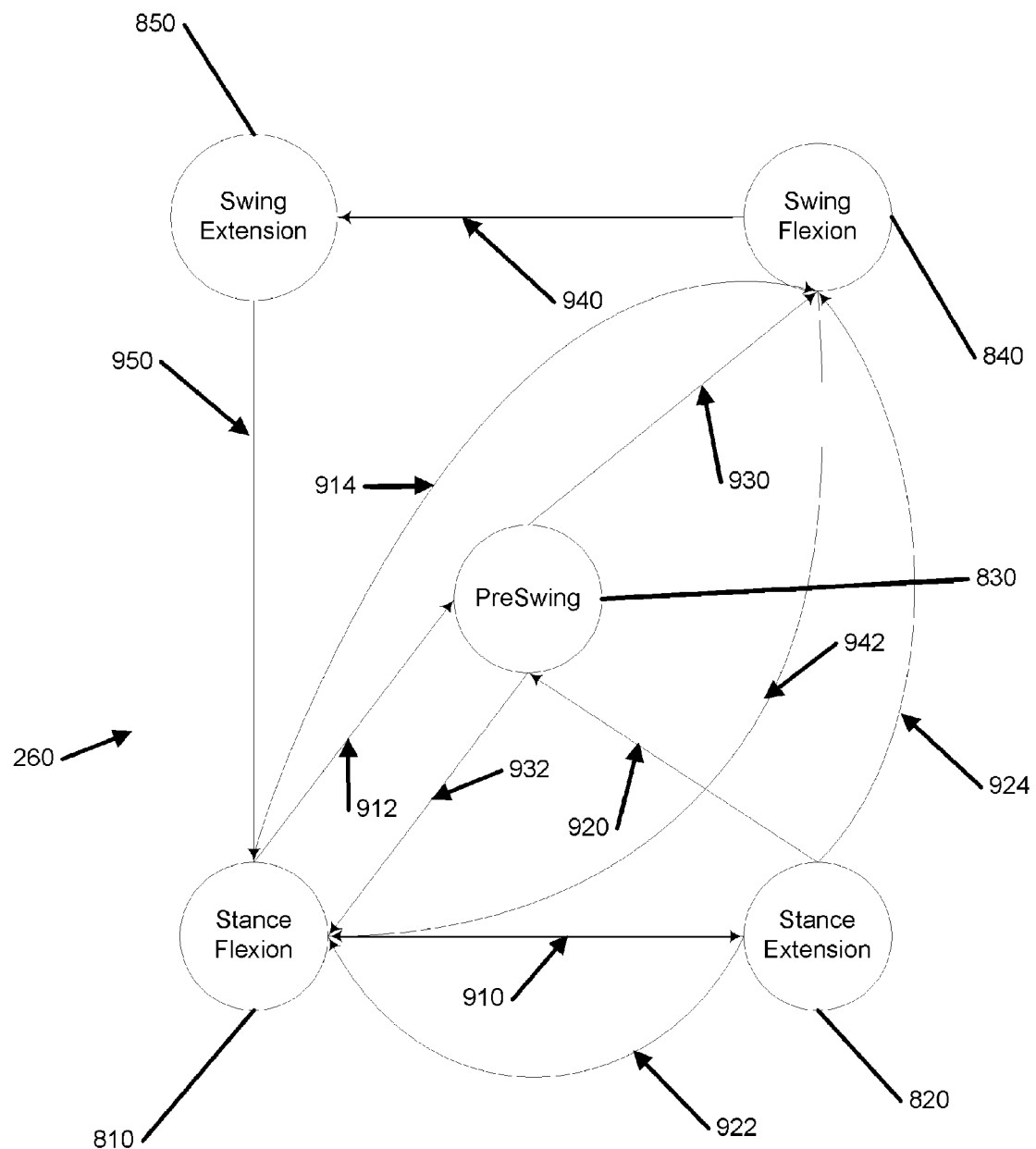
FIG. 9 is a more detailed state diagram depicting the specific state transitions in a control system such as depicted in FIG. 1.

The state machine transition and associated conditions recognized by one embodiment of the method 700 will now be discussed in more detail with respect to FIG. 9. One supported transition 910 is between the STF state 810 and the STE state 820. This state is recognized when the load sensors measurements indicate a loaded stance on the knee, the sign of the angular rate of change indicates that the knee has changed from flexing to extending, and when the knee has been in extension for a minimum time period. In one embodiment, this minimum time period is 20 ms.

A second transition 912 is a transition from the STF 810 state to the PS state 830. This may occur in amputees walking in the second pattern, discussed above. This transition may be guarded by several conditions to prevent inadvertent loss of knee support to the user. The transition may be recognized when a minimum period during which no substantial flexion or extension occurs, i.e., knee motion is within a small configurable threshold angle. In addition, the knee is preferably within 2 degrees of full extension and the knee extension moment is preferably a parameterized constant times an average of the maximum extension moment that is measured during operation. More preferably, the parameterized constant is 0.2. Preferably, the system 100 dynamically measures the maximum knee extension moment during every step, recalculates, and applies the stability factor for the next step. This advantageously provides dynamic stability calibration rather than a fixed calibration that is made by a prosthetist during configuration of the device. Dynamic stability control enables the system 100 to exhibit increased stance stability for the user while maintaining easy initiation of knee flexion during ambulation.

A third transition 914 is from the state 810 to the SWF state 840. This transition typically occurs on stair or ramps. During these activities, the knee sensors 106 detect a period of stance flexion followed by rapid unloading. At this point, the knee moves directly into a swing state without passing through the pre-swing state. Again, multiple conditions may be used to recognize this state to enhance stability for the user. First, the knee must be unloaded or the load must be less than linearly related to the maximum load measured during the present step. Preferably, this linear relation includes multiplying by a factor of 0.05. Second, the knee angle must be greater than a specified angle. Preferably, this specified angle is 10 degrees. Finally, the duration of the stance phase must be measured to be at least a specified time. Preferably, this specified time is approximately 0.23 s.

A transition 922 between the STE state 820 and the STF state 810 is also recognized. This state transition may occur during standing and walking. The transition is triggered by a change in direction of the knee movement during stance from stance extension to stance flexion. The transition may be delayed until the angular velocity of flexion exceeds a minimum value. Recognition of the transition 922 generally requires detection of an angular rate greater than a selected hysteresis value. Preferably, this selected value is approximately 10.

A transition 920 may be recognized between the STE state 820 and the PS state 830. The transition 920 may occur during weighted stance and generally occurs when the user is walking using stance flexion, as in the first, nominal, human walking pattern. In one embodiment, this transition may be recognized by the same conditions that are tested to recognize the transition 912.

Another transition 924 may be recognized between the STE state 820 and the SWF state 840. This transition 924 is typically a less frequent state transition that may occur when walking up stairs foot over foot. During this ambulation pattern, the knee reads a period of stance extension followed by rapid unloading. At this point, the knee moves directly into swing without moving into the pre-swing state. In one embodiment, this transition is recognized using the same conditions as used to recognize transition 914, discussed above.

Another transition 930 may be recognized between the PS state 830 and the SWF state 840. This transition represents the end of pre-swing and the beginning of initial swing. This is the point where low-level damping may be initiated to control heel rise. In one exemplifying embodiment, the knee is considered to be on the ground or weighted when the total force is greater than 5 kg for a period greater than 0.02 seconds. Otherwise, the foot is considered to be off the ground. This transition 930 is recognized when the knee is not on the ground or the angle of the knee must be greater than a specified angle. Preferably, this specified angle is 10°.

Another transition 932 may be recognized between the PS state 830 and the STF state 810. This is a safety transition intended to prevent inadvertent loss of support during stance when the user is not ready for swing. This implements a stumble recovery stance control feature of the system 100. The following conditions may be used to recognize the transition 932. The knee angle is greater than a specified angle. Preferably, the specified angle is 7 degrees. A calculated knee moment is greater than a specified fraction of an average maximum moment during extension. Preferably, this fraction is 0.01. Finally, the total force measured on the knee is greater than a fraction of the average total force on the knee. Note that in one embodiment, this average total force may be represented by a constant value, e.g., 19 kg.

A number of transitions from swing flexion, SWF state 840, may also be recognized. Transition 940 may be recognized between the state 840 and the SWE state 850. This transition 940 occurs during unloaded swing or may be triggered when a user is sitting so that little to no resistance to extension occurs during standing from a seated position. When walking, this transition is detected when the knee is extending and a filtered measure of angular velocity is greater than some non-calibrated minimum value. Preferably, this filtered measure is based on the infinite impulse filter described above. The minimum value is preferably less than −2. A condition on the non-filtered angular velocity may also be checked, e.g., whether the angular rate is less than a specified value. Preferably, the specified value is 10.

When sitting, a different set of conditions may be employed to recognize the transition 940. For example, the knee angle is greater than a specified angle. Preferably, this angle is 75° and the angular velocity is in a specified range of less, e.g., + or −1.5., i.e., the knee is relatively still.

A second transition from the SWF state 840 is a transition 942 to the state STF 810. This transition occurs when walking in small spaces or 'shuffling' feet. Recognition of the transition 942 generally accounts for some foot contact with the ground and may occur when: the knee must be considered loaded or 'on the ground', the knee angle is less than some specified angle, e.g., 20°, and the filtered velocity is less than a specified value, e.g., 5.

Transition 950 from the swing extension state 850 to the STF state 810 may be recognized. This is the normal transition from Swing to Stance. In one embodiment, two conditions are tested to recognize transition 950. First, the knee load sensor 106 reads at least a specified of total force, e.g., 5 kg, for a period greater than a specified time, e.g., 0.02 seconds. Second, the knee flexion angle is less than a specified angle. Preferably, this angle is 50°.

In addition to the above conditions, transition 950 may also occur with reference to one or more substates. In one embodiment, three substates are recognized within the SWE state 850. These states may be considered 'hold states' where the knee system 100 is programmed to apply torque at the end of terminal swing. The use of these substates may be configured using the graphical user interface described above. When certain conditions are met, the substate transitions become active and allow the knee to remain in extension for a fixed period at the end of swing phase. Preferably, this fixed period is approximately 4.5 seconds. This may enable a user to enter a vehicle easily without holding the shin of the prosthesis in extension during the transfer. This special feature eliminates the effect of gravity for a brief period of time that would otherwise cause the knee to move into flexion and cause an uncomfortable transfer process. Substate transitions preferably occur in the following order, Substate 1 to Substate 2 to Substate 3.

Substate 1 may be recognized during terminal swing where a positive velocity is found after terminal impact with a bumper in the knee. This Substate acts like an activation switch for initiation of the Substate transition sequences. The torque output is equal to that found in Swing Extension in Table 1, above. To recognize the transition to Substate 1 within the state 850, the angular velocity is measured as greater than zero, the knee angle is less than a specified angle, e.g., 30 degrees, and the user is not on stairs.

Substate 2 initiates active torque which provides an 'extension hold'. The damping during this state may be equal to a fraction of the STF 810 state damping multiplied by the absolute value of velocity plus a fixed 'hold' value. The transition to Substate 2 is recognized when the peak knee angle during swing phase is greater than a specified value, e.g., 20 degrees, the angular velocity is low, e.g., below a specified minimum, e.g., 5, and the knee angle must be less than some fixed constant angle, e.g., 2 degrees.

If the knee remains in Substate 2 for some fixed period of time, it will generally transition to Substate 3. Substate 3 prepares the knee system 100 for contact with the ground and loading. The damping output in this Substate may be equal to that in Substate 2 minus the fixed 'hold' value. The transition to Substate 3 is recognized when the time is greater than a specified hold time. This hold time may be configured using the graphical user interface described above. The initial value is preferably 4.5 seconds. In addition, the filtered velocity may be required to be greater than a specified value. In one embodiment, this value is 10.

Figure 10:
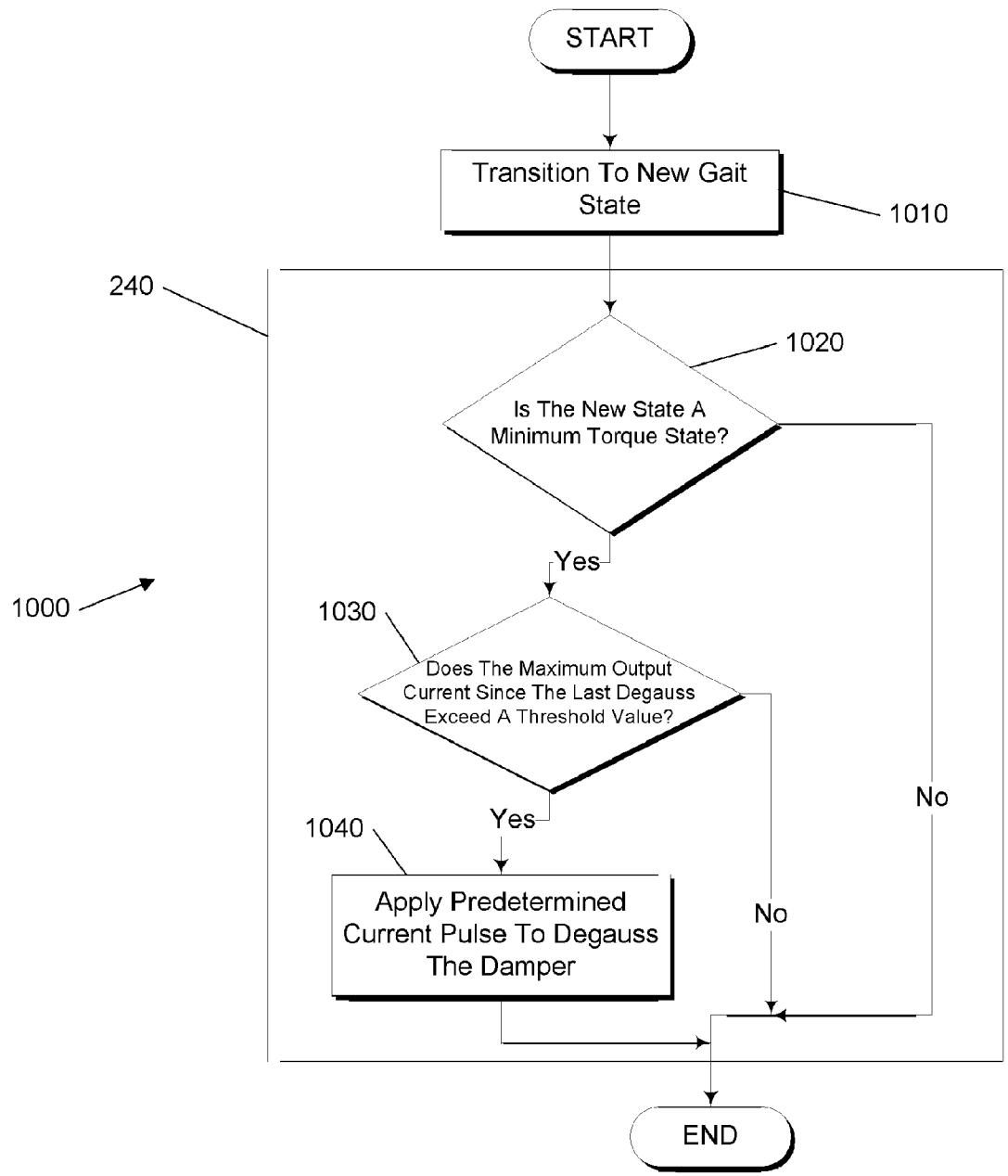
FIG. 10 is a flowchart depicting one embodiment of a method of minimizing residual magnetization in the actuator of a prosthetic control system such as depicted in FIG. 1.

FIG. 10 is a flowchart depicting one embodiment of a method 1000 of performing the degauss step 240 from FIG. 2. The method 1000 begins at step 1010 when a transition between states, as discussed above, is recognized. Next at decision step 1020, this new state is checked to determine if it is a minimum torque state. In one embodiment, the swing flexion 850 state, when stairs descent is detected, may be one such minimum torque state. If the state is not a minimum torque state, the method 1000 ends. If the state is a minimum torque state, the method 1000 proceeds to a step 1030. Next at the decision step 1030, a measure of the maximum applied output current is compared to a threshold current value. This threshold value may be configurable. If the threshold has not been exceeded, the method 1000 terminates. If the threshold has been exceeded, the method 1000 moves to step 1040. Next at step 1040, a current pulse is applied that is opposite in polarity to the current pulses that are applied to control damping of the actuator 108. In one embodiment, the magnitude of this reverse polarity pulse is based on the maximum damping current pulse that has been applied since the last execution of the method 1000. Preferably, this reverse polarity pulse is in the range of 10-50% of the maximum applied damping pulse. More preferably, the value of the reverse polarity pulse is approximately 25%. In other embodiments, the pulse may be 33%. Furthermore, the reverse polarity pulse amplitude may be greater or less than this fraction, or a fixed value depending on the electro-magnetic characteristics of a particular embodiment of the actuator 108.

Figure 11:
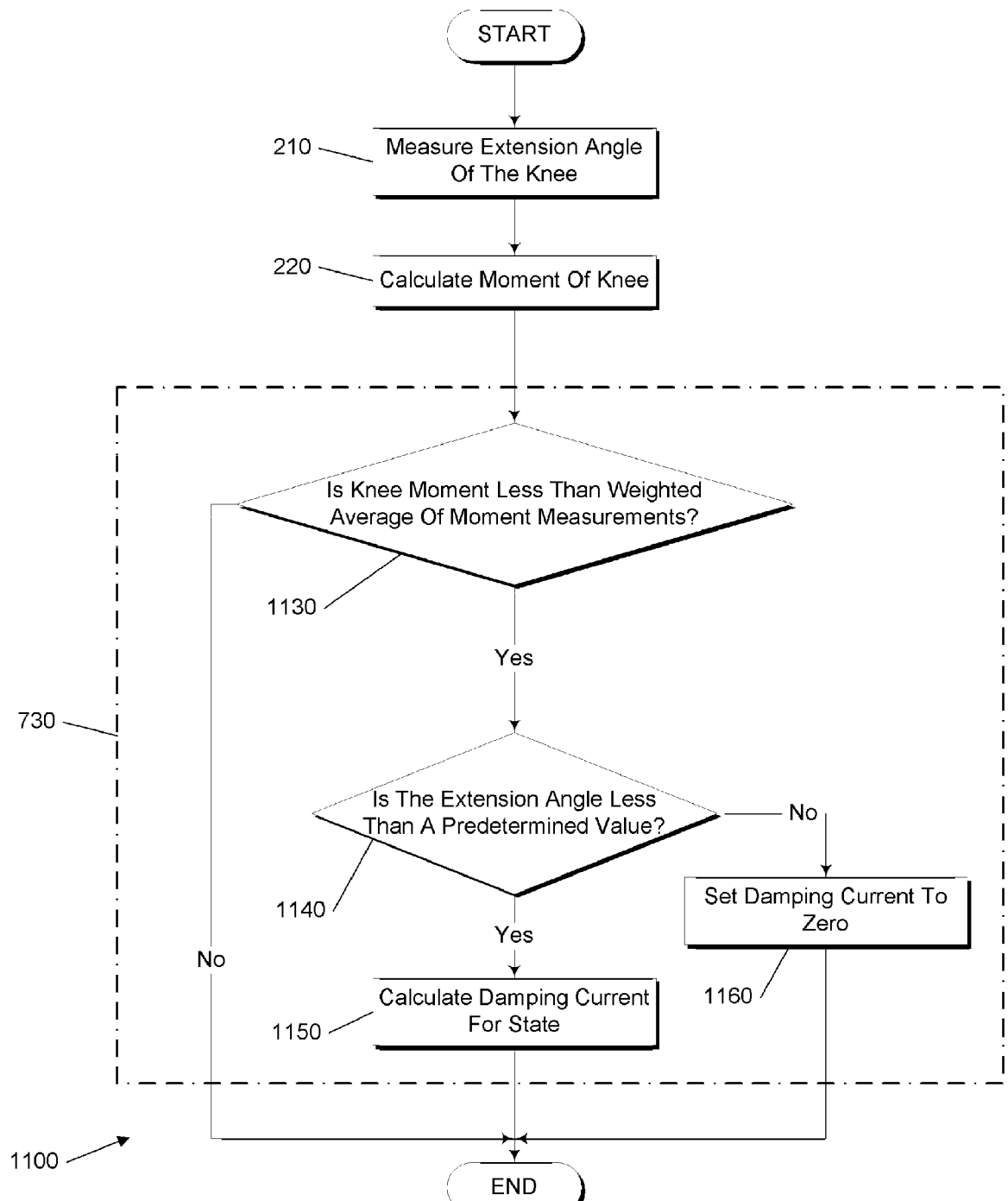
FIG. 11 is a flowchart depicting one embodiment of a method of controlling a prosthetic knee while climbing down an incline, e.g., stairs, in a control system such as depicted in FIG. 1.

In, for example, a knee embodiment of the prosthetic system 100, it may be advantageous to allow the knee to swing without damping when descending a ramp or stairs. FIG. 11 depicts one embodiment of a method 1100 for allowing the knee to swing freely when descending. The method 1100 is typically performed with respect to the gait state SWF 840. The method 1100 begins with the step 210, described with respect to the method 200, in which the knee extension angle is measured. Next at the step 220, the moment of the knee is calculated. The next set of steps 1130-1160 are now described with respect to the method 1100. However, it is to be appreciated that these steps may be performed at the step 730 of one embodiment of the method 700. Continuing at decision step 1130, the knee moment is compared to a weighted average of moment measurements. This average may, in some embodiments, be maintained over a period of steps, from power up, or over the lifetime of the particular system 100. If the knee moment is not less than the weighted average, the method 1100 ends. If the moment is greater, the method 1100 proceeds to step 1140. At decision step 1040, the measured extension angle of the knee is compared to a specified value. Preferably, this specified value may be configured using the user interface. In one embodiment, the default specified value is in the range of 3-7 degrees. If the angle is less than this specified angle, the method 1100 proceeds to step 1150. If the angle is greater than the specified angle, the method proceeds to step 1160. Moving to step 1150, the damping is calculated as described above for the current state and the method 1100 ends. Returning to step 1160, the damping value is set to be a value substantially less than the normally calculated value and the method 1100 terminates. Preferably, the damping value is set to be essentially zero.

Embodiments of the invention can efficaciously utilize other field responsive (FR) fluids and mediums. In one embodiment, an electrorheological (ER) fluid is used whose rheology can be changed by an electric (energy) field. Thus, the electrorheological (ER) fluid undergoes a rheology or viscosity change or variation which is dependent on the magnitude of the applied electric field. Other suitable electronically or electrically controlled or controllable mediums may be efficaciously utilized, as needed or desired.

Embodiments of the invention and the concepts disclosed, taught or suggested herein can be used in conjunction with other types of prosthetic knees and other prosthetic devices and joints including ankles, hips, elbows and wrists. Some embodiments of a prosthetic ankle are disclosed in U.S. patent application Ser. No. 11/056,344, filed Feb. 11, 2005, the entirety of which is hereby incorporated by reference herein.

In view of the above, one will appreciate that embodiments of the invention overcome many of the longstanding problems in the art by providing a prosthetic or orthotic control system that provides more natural and comfortable movement to its users. Moreover, this system enables more convenient and intuitive configuration through graphical computing devices. In addition, the system provides remote configuration and maintenance that allows for more efficient and flexible service to be provided to patients by reducing the need for in person visits to a prosthetist.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

What is claimed is:

1. A mobile computing device (MCD) configured to receive data from a prosthetic or orthotic device (P/O), the P/O having one or more moveable joints, a damper configured to control a resistance at the one or more moveable joints, an actuator associated with the damper to control movement or resistance at the one or more moveable joints, and a controller configured to operate the damper, the MCD comprising:
   a network interface configured to establish a wireless communication link directly with the P/O at least while the P/O is attached to a limb of a user and to receive from the P/O a first configuration parameter value associated with an adjustable configuration parameter of the P/O; and
   a processor communicatively coupled to the network interface and configured to:
   cause a display associated with the MCD to display an indicia of the first configuration parameter value;
   receive a second configuration parameter value based at least in part on a user interaction with the MCD; and
   cause the network interface to communicate the second configuration parameter value to the P/O, wherein the controller adjusts the adjustable configuration parameter based at least in part on the second configuration parameter value.

2. The device of claim 1, wherein the P/O has at least one of an ankle joint and/or a knee joint.

3. The device of claim 1, wherein the MCD comprises at least one of: a laptop, a phone, and or a personal digital assistant (PDA).

4. The device of claim 1, wherein the processor is further configured to:
   receive the first configuration parameter value from a network computing device.

5. The device of claim 1, wherein the processor is further configured to:
   calculate the second configuration parameter value for the P/O based at least in part on the one or more received P/O configuration parameters.

6. The device of claim 1, wherein the processor is further configured to cause the display to display a data entry control for the second configuration parameter value.

7. The system of claim 1, wherein the second configuration parameter value is a target value for the adjustable configuration parameter.

8. The system of claim 1, wherein the second configuration parameter value comprises one or more of: a target flexion angle, a swing angle, or a stance flexion angle.

9. The system of claim 1, wherein the adjustable configuration parameter is associated with a state machine condition.

10. The system of claim 1, wherein the processor is further configured to cause the network interface to communicate the second configuration parameter value to the P/O at least while the P/O is attached to the limb of the user.

* * * * *